United States Patent
Roth et al.

(10) Patent No.: US 11,504,398 B2
(45) Date of Patent: Nov. 22, 2022

(54) IDENTIFICATION OF CLONAL NEOANTIGENS AND USES THEREOF

(71) Applicant: Achilles Therapeutics UK Limited, London (GB)

(72) Inventors: Andrew Roth, Oxford (GB); Maximilian Prinz Zu Salm-Horstmar, London (GB); Fong Chun Chan, London (GB)

(73) Assignee: Achilles Therapeutics UK Limited, London (GB)

( * ) Notice: Subject to any disclaimer, the term of this patent is extended or adjusted under 35 U.S.C. 154(b) by 0 days.

(21) Appl. No.: 17/711,372

(22) Filed: Apr. 1, 2022

(65) Prior Publication Data

US 2022/0323499 A1   Oct. 13, 2022

(30) Foreign Application Priority Data

Apr. 1, 2021 (GB) ..................... 2104715

(51) Int. Cl.
*A61K 35/17* (2015.01)
*G16B 30/10* (2019.01)
(Continued)

(52) U.S. Cl.
CPC .......... *A61K 35/17* (2013.01); *A61K 39/0011* (2013.01); *A61P 35/00* (2018.01);
(Continued)

(58) Field of Classification Search
CPC ..... A61K 35/17; A61K 39/0011; A61P 35/00; C12Q 1/6886; C12Q 2600/106; C12Q 2600/156; G16B 30/10; G16H 20/10
See application file for complete search history.

(56) References Cited

U.S. PATENT DOCUMENTS

2018/0064793 A1\* 3/2018 Mcgranahan ........ G01N 33/505
2018/0251553 A1\* 9/2018 McGranahan ......... G16B 40/00
(Continued)

FOREIGN PATENT DOCUMENTS

CN           111785322 A    10/2020
WO    WO 2014/026096 A1    2/2014
(Continued)

OTHER PUBLICATIONS

Miller, Christopher A., et al. "SciClone: inferring clonal architecture and tracking the spatial and temporal patterns of tumor evolution." PLoS computational biology 10.8 (2014): e1003665. (Year: 2014).\*
(Continued)

*Primary Examiner* — Jesse P Frumkin
(74) *Attorney, Agent, or Firm* — Wolf, Greenfield & Sacks, P.C.

(57) ABSTRACT

A method of treating a subject having been diagnosed as having cancer with an immunotherapy is described. The method comprises targeting one or more clonal neoantigens selected using a method comprising determining whether a tumour-specific mutation is likely to be clonal in a subject. The method comprises providing sequence data from one or more samples from the subject comprising tumour genetic material, the sequence data comprising for each of the one or more samples, and determining the likelihood that the tumour-specific mutation is clonal as a posterior probability depending on: a prior probability of the mutation being clonal, and the probabilities of observing the sequence data if the tumour-specific mutation is (i) clonal and (ii) non-clonal, in view of a tumour fraction for each of the one or more samples and one or more candidate joint genotypes.

20 Claims, 13 Drawing Sheets

(51) Int. Cl.
*A61P 35/00* (2006.01)
*A61K 39/00* (2006.01)
*G16H 20/10* (2018.01)
*C12Q 1/6886* (2018.01)

(52) U.S. Cl.
CPC .......... *C12Q 1/6886* (2013.01); *G16B 30/10* (2019.02); *G16H 20/10* (2018.01); *C12Q 2600/106* (2013.01); *C12Q 2600/156* (2013.01)

(56) References Cited

U.S. PATENT DOCUMENTS

| | | | | |
|---|---|---|---|---|
| 2019/0172582 | A1* | 6/2019 | Onuchic | C12Q 1/6886 |
| 2020/0004925 | A1* | 1/2020 | Utro | G16B 40/00 |
| 2020/0032349 | A1* | 1/2020 | Espiritu | C12Q 1/6886 |
| 2021/0220455 | A1* | 7/2021 | Hacohen | A61K 39/0011 |
| 2021/0315983 | A1* | 10/2021 | Samuels | C12N 5/0693 |

FOREIGN PATENT DOCUMENTS

| | | | |
|---|---|---|---|
| WO | WO 2014/168874 | A2 | 10/2014 |
| WO | WO 2015/085233 | A1 | 6/2015 |
| WO | WO 2015/095811 | A1 | 6/2015 |
| WO | WO 2016/174085 | A1 | 11/2016 |
| WO | WO 2016/201049 | A2 | 12/2016 |
| WO | WO 2019/012296 | A1 | 1/2019 |

OTHER PUBLICATIONS

British Search Report for British Application No. 2104715.4 dated Sep. 27, 2021.
Carter et al., Absolute quantification of somatic DNA alterations in human cancer. Nature biotechnology. May 2012;30(5):413-21.
Landau et al., Evolution and impact of subclonal mutations in chronic lymphocytic leukemia. Cell. Feb. 14, 2013;152(4):714-26.
Toosi et al., BAMSE: Bayesian model selection for tumor phylogeny inference among multiple samples. BMC Bioinformatics. Jun. 2019;20(11):95-103.
[No Author Listed], HaplotypeCaller. Gatx. 2022. 43 pages. https://gatk.broadinstitute.org/hc/en-us/articles/360037225632-HaplotypeCaller [Last accessed Apr. 19, 2022].
[No Author Listed], TracerX. Tracking Cancer Evolution through Study. 2022. 2 pages. http://tracerx.co.uk/ [Last accessed Apr. 19, 2022].
Adalsteinsson et al., Scalable whole-exome sequencing of cell-free DNA reveals high concordance with metastatic tumors. Nature communications. Nov. 6, 2017;8(1). 13 pages.
Bulik-Sullivan et al., Deep learning using tumor HLA peptide mass spectrometry datasets improves neoantigen identification. Nature Biotechnology. Jan. 2019;37(1):55.
Farahani et al., Engineered in-vitro cell line mixtures and robust evaluation of computational methods for clonal decomposition and longitudinal dynamics in cancer. Scientific reports. Oct. 18, 2017;7(1). 13 pages.
Gillis et al., PyClone-VI: scalable inference of clonal population structures using whole genome data. BMC Bioinformatics. Dec. 2020;21(1). 16 pages.
Jurtz et al., NetMHCpan-4.0: improved peptide-MHC class I interaction predictions integrating eluted ligand and peptide binding affinity data. The Journal of Immunology. Nov. 1, 2017;199(9):3360-8.
Langmead et al., Ultrafast and memory-efficient alignment of short DNA sequences to the human genome. Genome biology. Mar. 2009;10(3):1-0.
Litchfield et al., Meta-analysis of tumor-and T cell-intrinsic mechanisms of sensitization to checkpoint inhibition. Cell. Feb. 4, 2021;184(3):596-614.
Lundegaard et al., NetMHC-3.0: accurate web accessible predictions of human, mouse and monkey MHC class I affinities for peptides of length 8-11. Nucleic acids research. Jul. 1, 2008;36(suppl_2):W509-12.
McGranahan et al., Clonal neoantigens elicit T cell immunoreactivity and sensitivity to immune checkpoint blockade. Science. Mar. 25, 2016;351(6280). 13 pages.
McGranahan et al., Clonal status of actionable driver events and the timing of mutational processes in cancer evolution. Science translational medicine. Apr. 15, 2015;7(283). 22 pages.
O'Donnell et al., MHCflurry: open-source class I MHC binding affinity prediction. Cell systems. Jul. 25, 2018;7(1):129-32.
Raine et al., ascatNgs: Identifying somatically acquired copy-number alterations from whole-genome sequencing data. Current protocols in bioinformatics. Dec. 2016;56(1). 24 pages.
Roth et al., PyClone: statistical inference of clonal population structure in cancer. Nature methods. Apr. 2014;11(4). 14 pages.
Schwartz et al., The evolution of tumour phylogenetics: principles and practice. Nature Reviews Genetics. Apr. 2017;18(4). 35 pages.
Van Loo et al., Allele-specific copy number analysis of tumors. Proceedings of the National Academy of Sciences. Sep. 28, 2010;107(39):16910-5.
International Search Report and Written Opinion for International Application No. PCT/EP2022/058793 dated Jul. 29, 2022.

* cited by examiner

IDENTIFICATION OF CLONAL NEOANTIGENS AND USES THEREOF

CROSS REFERENCE TO RELATED APPLICATIONS

This application claims priority under 35 U.S.C. § 119 (a)-(d) of United Kingdom application number GB 2104715.4, filed Apr. 1, 2021, which is incorporated by reference herein in its entirety.

FIELD OF THE DISCLOSURE

The present disclosure relates to methods for determining whether a tumour-specific mutation is likely to be clonal and for identifying clonal neoantigens derived from tumour-specific mutations present in a tumour. The present disclosure also relates to methods and compositions for the treatment of cancer which make use of or target identified clonal neoantigens.

BACKGROUND

Cancer cells are known to acquire mutations, some of which may confer evolutionary advantages. As a result, tumours often comprise multiple genotypically distinct, related populations (or clones). Characterising a tumour's clonal composition is particularly important in a therapeutic context. Indeed, targeting mutations that are present only in subsets of the tumour cell population (also referred to as "subclonal" mutations) may be associated with limited clinical benefit as the therapy only targets part of the population and a high likelihood of relapse or metastasis as unaffected clones remain able to proliferate. Instead, it is increasingly believed that targeting clonal neoantigens (antigens expressed as a result of the presence of mutations that are present in all tumor cells) or combining multiple targeted therapies may be necessary to effectively control a tumour (McGranahan et al., 2015). Additionally, clonal neoantigen burden is known to be associated with prognosis in at least some cancers, and with sensitivity to treatment with checkpoint inhibitors (McGranahan et al., 2016; Litchfield et al., 2021).

SUMMARY

The present inventors have developed a new method for determining whether a tumour-specific mutation is likely to be clonal using sequence data from one or more samples comprising tumour cells or genetic material derived therefrom that addresses one or more of the problems of prior art approaches. This method finds particular use in identifying clonal neoantigens, for example for the purpose of cancer therapy or prognosis. The method uses a rigorous statistical framework to classify individual mutations as clonal, and provides a probability reflecting the confidence in the assignment. The method is fast, flexible, robust and replicable, relies on interpretable assumptions, can flexibly incorporate somatic copy number aberration data and can take into account uncertainty in copy number calls due to multiple ploidy/purity solutions in providing its predictions.

Thus, according to a first aspect, there is provided a method of determining whether a tumour-specific mutation is likely to be clonal in a subject, the method comprising: providing, or obtaining, sequence data from one or more samples from the subject comprising tumour genetic material, the sequence data comprising for each of the one or more samples, at least two of: the number of reads in the sample that show the tumour-specific mutation ($d_b$), the number of reads in the sample that show the corresponding germline allele, and the total number of reads at the location of the tumour-specific mutation (d); and determining the likelihood that the tumour-specific mutation is clonal as a posterior probability depending on: a prior probability of the mutation being clonal, and the probabilities of observing the sequence data if the tumour-specific mutation is (i) clonal and (ii) non-clonal, in view of a tumour fraction for each of the one or more samples and one or more candidate joint genotypes each comprising a genotype at the location of the tumour-specific mutation for a normal population, a reference tumour population that does not comprise the tumour-specific mutation and a variant tumour cell population that comprises the tumour-specific mutation.

The method obtains a probability that a mutation is clonal ($P(Z=1)$) as a posterior probability ($p(Z=1|d_b, d, \pi, t, \rho)$) that depends on the prior probability of the mutation being clonal ($\rho$), and the probability of observing the sequence data (also referred to as the "likelihood" of observing the sequence data, or simply the "likelihood" of the sequence data). Thus, it can be obtained separately for any mutation simply using the sequence data that relates to the mutation under investigation, and produces a readily interpretable output that relies on explicit assumptions (i.e. the prior probability of the mutation being clonal, and the likelihood of observing the sequence data in view of an explicit model of population structure). In other words, such a probability is dependent on both the data available from one or more samples comprising tumour genetic material, and on any prior knowledge available, through a Bayesian framework underlined by a rigorous set of assumptions that can be checked. This output can be used to compare, e.g. prioritize, any number of mutations, which need not cover a whole genome. It also has the ability to combine evidence from multiple samples comprising tumour genetic material but can equally be determined using a single sample comprising tumour genetic material.

The method of the present aspect may have one or more of the following features.

The method may be computer implemented. Thus, the step of obtaining the sequence data may be performed by a processor, and the step of determining the likelihood that the tumour-specific mutation is clonal may be performed by said processor. The step of obtaining the sequence data may comprise receiving sequence data comprising sequence reads from one or more samples from the subject, and determining from said sequence reads at least two of: the number of reads in the sample that show the tumour-specific mutation ($d_b$), the number of reads in the sample that show the corresponding germline allele, and the total number of reads at the location of the tumour-specific mutation (d). At least the step of determining the likelihood that the tumour-specific mutation is clonal may be computer implemented. The step of determining the likelihood that the tumour-specific mutation is clonal may comprise a step of numerical integration to obtain the posterior probability. In particular, the step may comprise determining the posterior probability that the mutation is clonal in view of a prior probability of the mutation being clonal, and the probabilities of observing the sequence data if the tumour-specific mutation is (i) clonal and (ii) non-clonal, by solving a plurality of one dimensional integrals (such as e.g. a pair of integrals for each sample, respectively representing the assumption that the mutation is clonal and non-clonal) integrating the probability of the observed sequence data over all possible cancer cell fractions between 0 and 1. These numerical integrals may be solved independently (such as e.g. in parallel) for each sample and each mutation. The step of providing may comprise one or more steps, all or some of which are computer implemented.

The probability that the tumour-specific mutation is clonal may depend on the prior probability of the mutation being clonal ($\rho$) through: a prior probability of the mutation being assigned to a clonal category given the prior probability of the mutation being clonal ($P(Z=1|\rho)=\rho$); and a prior probability of the mutation being assigned to a non-clonal category given the prior probability of the mutation being clonal ($P(Z=0|\rho)=(1-\rho)$). The probability of observing the sequence data if the tumour-specific mutation is clonal (in view of a tumour fraction for each of the one or more samples and one or more candidate joint genotypes) may be marginalised over the cancer cell fraction. Similarly, the probability of observing the sequence data if the tumour-specific mutation is not clonal, in view of a tumour fraction for each of the one or more samples and one or more candidate joint genotypes, may be marginalised over the cancer cell fraction.

The probability that the tumour-specific mutation is clonal may depend on: the prior probability of the mutation being assigned to a clonal category given the prior probability of the mutation being clonal ($P(Z=1|\rho)=\rho$), multiplied by the probability in each sample of observing the sequence data in view of a tumour fraction, and one or more candidate joint genotypes, if the mutation is clonal (which can be calculated as $\psi_1$, the likelihood of the sequence data in each sample, marginalised over the cancer cell fraction); and the prior probability of the mutation being assigned to a non-clonal category given the prior probability of the mutation being subclonal ($P(Z=0|\rho)=1-\rho$), multiplied by the probability in each sample of observing the sequence data in view of a tumour fraction and one or more candidate joint genotypes, if the mutation is non-clonal (which can be calculated as $\psi_0$, the likelihood of the sequence data in each sample, marginalised over the cancer cell fraction).

The probability that the tumour specific mutation is clonal may be obtained as the ratio of (i) the prior probability of the mutation being assigned to a clonal category given the prior probability of the mutation being clonal multiplied by the probability of observing the sequence data in each sample in view of a tumour fraction and one or more candidate joint genotypes, if the mutation is clonal ($p(d_b, d, Z=1|\pi,t, \rho)$, which can be expressed as $\rho\psi_1$), divided by (ii) the sum of (i) (i.e. $p(d_b, d, Z=1|\pi,t, \rho)$) and the prior probability of the mutation being assigned to a non-clonal category given the prior probability of the mutation being subclonal, multiplied by the probability of observing the sequence data in each sample view of a tumour fraction in each sample and one or more candidate joint genotypes, if the mutation is non-clonal ($p(d_b, d, Z=0|\pi,t, \rho)$, which can be expressed as $(1-\rho)\psi_0$).

The probability that a mutation is clonal may be obtained using equation (11a). In equation (11a), the term $Pr(d_b,d|\pi, \phi, t)$ may be given by any of equations (3), (4), (3a), (4a), (3b) or (4b). In equation (11), the terms $p(\phi|Z=0)$ and $p(\phi|z=1)$ may be given by equation (6).

A clonal mutation may be a mutation that is present in all or essentially all tumour cells in the one or more samples from the subject comprising tumour genetic material (or in all of the tumour genetic material in the one or more samples). Such a mutation may be, or may be assumed to be (as full certainty on this may be associated with sequencing of all tumour cells in the subject, but presence in essentially all cells in one or more samples may be used as an indication of this), present in all tumour cells in the subject.

The probability of observing the sequence data in view of a tumour fraction in each sample and one or more candidate joint genotypes may depend on the probability of observing the sequence data in view of a tumour fraction, cancer cell fraction and one or more candidate joint genotypes ($Pr(d, db|\pi, \phi, t)$). The probability of observing the sequence data in view of a tumour fraction, cancer cell fraction and one or more candidate joint genotypes may be a weighted sum of the probabilities of observing the sequence data in view of a tumour fraction, cancer cell fraction and each of the one or more candidate joint genotypes.

Advantageously, the probability of observing the sequence data (likelihood of the sequence data) may be calculated over a plurality of candidate genotypes (e.g. as a sum of probabilities comprising a term for each candidate genotype, see e.g. equations (3a), (3b)), the contribution of which may be weighted for example to reflect prior knowledge on the relative probabilities of the candidate genotypes (e.g. any prior knowledge on whether some genotypes are more likely to occur than others). When no such prior knowledge is available or desirable, the probabilities for each of the candidate genotypes may be weighted equally. The weights of the respective candidate genotypes considered suitably sum to 1, such that the total probability reflects the relative contributions of the different candidate joint genotypes considered. When a single candidate joint genotype is used, it may be assigned a weight of 1 (i.e. no sum may be obtained).

The probability of observing the sequence data in view of a tumour fraction, cancer cell fraction and a particular candidate joint genotype ($G_i$) (which can be calculated as $\psi_z$, the likelihood of the sequence data in each sample, marginalised over the cancer cell fraction) may be obtained using a Binomial distribution with parameters $d_b$ and $\xi(G_i, \phi, t)$. Alternatively, the probability of observing the sequence data in view of a tumour fraction, cancer cell fraction and a particular candidate joint genotype may be obtained using a BetaBinomial distribution with parameters $d_b$, $\xi(G_i, \phi, t)$, and $\gamma$. In both cases (i.e. whether a Binomial or a BetaBinomial distribution is used), $\xi(G_i, \phi, t)$ may represent the probability of sampling a read with the variant allele assuming a particular genotype Gi, a cancer cell fraction $\phi$ and a tumour purity t. The probability $\xi(G_i, \phi, t)$ may be obtained as a function of the total number of copies for each of the normal, variant and reference genotypes, the probability of sampling a read with the variant from a population with genotype Gi in view of the proportion of alleles at the locus that are variant in the genotype and the sequencing error rate, the tumour fraction in the sample and the cancer cell fraction for the mutation.

The probability of observing the sequence data in view of a tumour fraction in each sample and one or more candidate joint genotypes may be obtained as an integral over all possible values of the cancer cell fraction in each sample, wherein the cancer cell fraction is the proportion of tumour cells that comprise the tumour-specific mutation. Thus, the step of determining the likelihood that the tumour-specific mutation is clonal may comprise using a processor to numerically integrate said integral.

The cancer cell fraction ($\phi$) may take values between 0 and 1. In other words, the probability of observing the sequence data in view of a tumour fraction in each sample and one or more candidate joint genotypes, if the mutation is clonal or non-clonal may be obtained by integrating a value that is dependent on the cancer cell fraction over all possible values of the cancer cell fraction (i.e. marginalising over the cancer cell fraction). The value that is dependent on the cancer cell fraction may be expressed as $\Pr(d_b, d|\pi, \phi, t)p(\phi|Z=z)$ where the first term is the probability of observing the sequence data in view of a tumour fraction, cancer cell fraction and one or more candidate joint genotypes, and the second term is the prior probability (i.e. a probability based on assumptions of how the cancer cell fraction should behave for a clonal/non-clonal mutation) of a cancer cell fraction if the mutation is classified as clonal or non-clonal (Z=1 or Z=0, respectively). Thus, the probability of observing the sequence data in view of a tumour fraction in each sample and one or more candidate joint genotypes may be obtained as $\int_0^1 \Pr(d_b, d|\pi, \phi, t)p(\phi|Z=z)d\phi$.

The prior probability of a particular cancer cell fraction if the mutation is classified as clonal may be defined as a beta distribution with parameters $\alpha$ (set to a value>1, for example, 99, though any other value may be used) and $\beta=1$ (Beta($\phi|\alpha$, 1)). The prior probability of a particular cancer cell fraction if the mutation is classified as non-clonal may be defined as a beta distribution with parameters $\alpha=1$ and $\beta=1$ (Beta($\phi|1,1$)).

Sequence data from a plurality of samples may be obtained and the probability of observing the sequence data in view of a tumour fraction for each of the plurality of samples and one or more candidate joint genotypes may be obtained as the product of the probability of observing the sequence data of each sample in view of the tumour fraction in the respective sample and the one or more candidate joint genotypes.

Advantageously, the present method is able to seamlessly integrate evidence for/against the clonality of a mutation obtained from multiple samples if these are available. This is particularly advantageous as methods for inferring the clonal structure of tumour cell populations that can utilise multi-region sequencing data have been shown to perform particularly well in benchmarking studies (Farahani et al., 2017).

The method may further comprise obtaining or providing, for each sample, at least one estimate of the tumour fraction, and at least one corresponding set of one or more candidate joint genotypes. A tumour fraction estimate may be obtained using a method for determining allele-specific copy number profiles in samples comprising a mixture of tumour and normal cells. Methods for doing this using sequencing or array data are known in the art, for example by expressing the allele specific data as a function of parameters including allele-specific copy numbers, tumor aneuploidy and tumor cell fraction, and identifying the value of these parameters that best fit all of the data. Examples of such methods include e.g. ASCAT (Van Loo et al., 2010), amongst others. Alternatively, a tumour fraction estimate may be determined experimentally. Thus, the method may further comprise obtaining a tumour fraction estimate for each of the one or more samples. In particular, the method may comprise obtaining, by a processor, for each sample, at least one estimate of the tumour fraction comprises the processor determining an estimate of the tumour fraction and allele specific copy numbers using the sequence data, and determining, by said processor, a set of one or more candidate joint genotypes associated with said allele specific copy numbers.

A set of one or more candidate genotypes may be obtained using allele-specific copy numbers or variables derived therefrom (or conversely, from which such allele-specific copy numbers can be derived, such as B allele fraction and log R) for the tumour cells in a mixed sample. Allele-specific copy numbers for the tumour cells in a mixed sample may be obtained using a method for determining allele-specific copy number profiles in samples comprising a mixture of tumour and normal cells, such as e.g. ASCAT (Van Loo et al., 2010), or ascatNgs (Raine et al., 2016), amongst others.

Thus, the method may further comprise obtaining, for each of the one or more samples, estimates for at least two of: the copy number of the major allele in the tumour cells in the sample, the copy number of the minor allele in the tumour cells in the sample, and the total copy number at the location of the tumour-specific mutation in the tumour cells in the sample. The estimates of copy number in the tumour cells in the sample may represent a summarised (e.g. average) estimate over the entire population of tumour cells in the sample.

A set of one or more candidate joint genotypes may be obtained as the candidate joint genotypes that are compatible with the assumptions that: the normal population only comprises the normal allele(s) A(i.e. $G_H$=AA or A, e.g. if the locus is on a sex chromosome); the reference population does not comprise the variant allele B (i.e. $G_R$=(A)*n); and the variant population comprises at least one copy of the variant allele B (i.e. $G_V$=(A)*m(B)*l).

Advantageously, the set of candidate genotypes may comprise the candidate joint genotypes that are further compatible with the assumptions that either: (i) the reference population genotype matches the normal population genotype and the variant population has a copy number equal to the total copy number at the location and up to the major copy number of the variant allele; or (ii) the reference population has a copy number equal to the total copy number at the location and the variant population has 1 variant allele and a copy number equal to the total copy number at the location ("major copy number prior"). This approach advantageously strikes a good balance between accounting for uncertainty in the genotypes of the populations while not considering too many states.

Instead or in addition to this, a set of one or more candidate joint genotypes may comprise any of the candidate joint genotypes that are compatible with the assumption that: each mutation is diploid and heterozygous (i.e. $G_V$=AB, $G_R$=AA) ("AB prior"). Instead or in addition to this, a set of one or more candidate joint genotypes may comprise any of the candidate joint genotypes that are compatible with the assumption that: each mutation is diploid and homozygous (i.e. $G_V$=BB, $G_R$=AA) ("BB prior"). Instead or in addition to this, a set of one or more candidate joint genotypes may comprise any of the candidate joint genotypes that are compatible with the assumption that: the genotype of the variant population has the predicted total copy number at the region of the mutation, with exactly one mutant allele (i.e. $G_V$=(A)*mB where m=total copy number −1) ("no zygosity prior"). Instead or in addition to this, a set of one or more candidate joint genotypes may comprise any of the candidate joint genotypes that are compatible with the assumption that: the genotype of the variant population has the predicted total copy number at the region of the mutation, with at least one mutant allele, and the reference population is either AA or the genotype with a copy number equal to the predicted total copy number and no variant allele (i.e. $G_R$=(A)*n where n is the total copy number, $G_V$=(A)*m(B)*l where m+l=n and l>1) ("total copy number prior"). Instead or in addition to this, a set of one or more candidate joint genotypes may comprise any of the candidate joint genotypes that are compatible with the assumption that: the genotype of the variant population has a number of mutant alleles corresponding to either the major copy number or the minor copy number ("parental mode").

The probability of observing the sequence data may combine a plurality of probabilities of observing the sequence data in view of a respective tumour fraction and a corresponding set of one or more candidate joint genotypes for at least one of the one or more samples, optionally wherein the method comprises obtaining, for at least one or the one or more samples, a plurality of estimates of the tumour fraction, and a plurality of corresponding sets of one or more candidate joint genotypes. Thus, the method may comprise obtaining, for at least one sample, a plurality of estimates of the tumour fraction. This may comprise comprises determining, by a processor, a plurality of estimates of the tumour fraction and a corresponding plurality of allele specific copy numbers that are compatible with the sequence data, and determining, by the processor, a plurality of sets of one or more candidate joint genotypes associated with said plurality of allele specific copy numbers.

The present method is advantageously able to determine a probability of a mutation being clonal which takes into account a plurality of possible tumour fractions and corresponding sets of candidate joint genotypes. In other words, the present method is able to obtain a probability of a mutation being clonal which integrates over a plurality of copy number solutions from which tumour fractions and candidate joint genotypes can be obtained. By contrast, prior art approaches typically rely on a single estimate of tumour purity and allele-specific copy numbers (from which candidate joint genotypes can be obtained), which is often manually selected according to expert defined optimality criteria. The step of selecting a copy number solution that is deemed optimal is highly error prone, and the output of methods that rely on single solutions is likely to change significantly depending on the solution.

Thus, advantageously, the probability of observing the sequence data (likelihood of the sequence data) may be calculated over a plurality of sets of candidate genotypes and corresponding tumour fraction estimates (e.g. as a sum of probabilities comprising a term for each copy number solution, see equations (3b), (4b)), the contribution of which may be weighted for example to reflect the confidence in the copy number solution from which the tumour fraction estimate and set of candidate genotypes were obtained. The weights of the contributions of the copy number solutions considered suitably sum to 1, such that the total probability reflects the relative contributions of the different copy number solutions considered. When a single copy number solution is used, it may be assigned a weight of 1 (i.e. no sum may be obtained).

The prior probability of the mutation being clonal may be set to a neutral prior, or to a value derived from prior data and/or expert knowledge. Advantageously, the methods described herein are able to take prior knowledge about a mutation into account in the Bayesian framework used to determine the probability of a mutation being clonal, if such knowledge is available. However, they are also able to provide a likelihood of a mutation being clonal even in the absence of such knowledge.

A value for the prior probability of the mutation being clonal may depend on the subject, tumour, the mutation, or a combination of these. For example, a value may be determined using data previously acquired on a relevant cohort of patients, such as e.g. patients that suffer from the same type or subtype of cancers. For example, knowledge of the proportion of mutations that are clonal vs. subclonal in such a cohort may be used to set the prior probability used herein. Alternatively, a value may be set arbitrarily based on prior knowledge about the cancer type or mutation. For example, specific mutations that have been found across a plurality of cancer samples and have been identified as often being clonal in these samples may be assigned a higher than 0.5 probability.

The method may further comprise repeating the method for a plurality of tumour-specific mutations identified in the subject. The method may further comprise ranking or otherwise prioritising the plurality of tumour-specific mutations at least in part based on their determined likelihood of being clonal in the subject.

The method may further comprise identifying one or more tumour-specific mutations in the subject. Identifying one or more tumour-specific mutations in the subject may be performed using sequence data from one or more samples from the subject comprising tumour genetic material and sequence data from one or more germline samples from the subject, such as by comparing said sequence data. Identifying one or more tumour-specific mutations in the subject may comprise aligning sequence data from at least one sample comprising tumour genetic material to a reference sequence and identifying positions where the sequence of the sample differs from the reference sequence. The method may further comprise aligning sequence data from at least one germline sample to the reference sequence and identifying positions where the sequence of the sample comprising tumour genetic material differs from the germline sample.

The step of providing sequence data from one or more samples from the subject may comprise or consist of receiving sequence data from a user (for example through a user interface), from one or more computing device(s), or from one or more data stores or databases.

The step of providing sequence data may further comprise sequencing (or otherwise determining the sequence composition of genomic material present in a sample) one or more samples from the subject comprising tumour genetic material.

The method may further comprise sequencing (or otherwise determining the sequence composition of genomic material present in a sample) one or more germline samples from the subject.

The method may further comprise obtaining, from the subject, one or more samples comprising tumour genetic material and optionally one or more germline samples.

The method may further comprise providing to a user, for example through a user interface, the determined probability of the tumour-specific mutation being clonal and/or a value derived therefrom or associated therewith. For example, the method may comprise providing a "clonal status" flag or value based on the determined probability of the tumour-specific mutation being clonal. As another example, the method may comprise providing information identifying the mutation (such as e.g. the sequence of the mutation and its genomic location).

According to a further aspect, there is provided a method of identifying one or more clonal neoantigens in a subject, the method comprising: identifying a plurality of tumour-specific mutations in the subject; determining whether one or more of the tumour-specific mutations is likely to be clonal in the subject using the method of any embodiment of the preceding aspect; and determining whether one or more of the tumour-specific mutations is likely to give rise to a neoantigen, wherein a clonal neoantigen is a tumour-specific mutation that satisfies one or more predetermined criteria on whether the tumour-specific mutation is likely to be clonal and one or more criteria on whether the tumour-specific mutation is likely to give rise to a neoantigen. Also described according to the present aspect is a method of identifying one or more clonal neoantigens in a subject, the method comprising: identifying, by a processor using sequence data from one or more samples from said subject, a plurality of tumour-specific mutations in the subject; determining, by a processor whether one or more of the tumour-specific mutations is likely to be clonal in the subject using the method of any preceding claim; and selecting, by said processor, one or more of the tumour-specific mutations as candidate clonal neoantigens, wherein a candidate clonal neoantigen is a tumour-specific mutation that satisfies at least one or more predetermined criteria on whether the tumour-specific mutation is likely to be clonal and optionally one or more criteria on whether the tumour-specific mutation is likely to give rise to a neoantigen.

The method of the present aspect may have any one or more of the following features.

A clonal neoantigen may be a tumour-specific mutation that satisfies at least a criterion selected from: having a probability of being clonal above a predetermined threshold, having a probability of being clonal that is above a threshold set adaptively to select a predetermined number of tumour-specific mutations with the highest probabilities of being clonal amongst the tumour-specific mutations for which a probability was determined, and having a probability of being clonal that is above a threshold set adaptively to select a predetermined top percentile of tumour-specific mutations amongst the tumour-specific mutations for which a probability was determined. Thus, the one or more predetermined criteria on whether the tumour-specific mutation is likely to be clonal may be selected from: the mutation having a likelihood of being clonal above a predetermined threshold, the mutation having a likelihood of being clonal that is above a threshold set adaptively to select a predetermined number of tumour-specific mutations with the highest likelihoods of being clonal amongst the tumour-specific mutations for which a likelihood was determined, and having a likelihood of being clonal that is above a threshold set adaptively to select a predetermined top percentile of tumour-specific mutations amongst the tumour-specific mutations for which a likelihood was determined.

A clonal neoantigen may be a tumour-specific mutation that satisfies at least a criterion selected from: being associated with an expression product that is expressed in tumour cells, being predicted to result in a protein or peptide that is not expressed in the normal cells of the subject, being predicted to result in at least one peptide that is likely to be presented by an MHC molecule, being predicted to result in at least one peptide that is likely to be presented by an MHC allele that is known to be present in the subject, and being predicted to result in a protein or peptide that is immunogenic. For example, a clonal neoantigen may be a tumour-specific mutation that satisfies a criterion that it is predicted to result in a change in the sequence of a protein (e.g. because it is coding, because it affects a splice site, because it results in a truncated peptide, etc.), thus resulting in a protein or peptide that may not be expressed in the normal cells of the subject. Whether or not this is the case may further be confirmed for example by comparison with a predicted normal proteome of the subject. Thus, the one or more criteria on whether the tumour-specific mutation is likely to give rise to a neoantigen may be selected from: the mutation being associated with an expression product that is expressed in tumour cells, the mutation being predicted to result in a protein or peptide that is not expressed in the normal cells of the subject, the mutation being predicted to result in at least one peptide that is likely to be presented by an MHC molecule, the mutation being predicted to result in at least one peptide that is likely to be presented by an MHC allele that is known to be present in the subject, and the mutation being predicted to result in a protein or peptide that is immunogenic.

The method may further comprise identifying one or more peptides associated with the one or more clonal neoantigens (i.e. one or more peptide sequences that are predicted to be present in the tumour cells as a consequence of the presence of the tumour-specific mutation, where the tumour-specific mutation satisfies one or more criteria (related to likelihood of clonality and likelihood of giving rise to a clonal neoantigen) as described above.

As the skilled person understands, the complexity of the operations described herein (due at least to the complexity of obtaining posterior probabilities requiring numerical integration as described herein, and the amount of data that is typically generated by sequencing genomic DNA) are such that they are beyond the reach of a mental activity. Thus, unless context indicates otherwise (e.g. where sample preparation or acquisition steps are described), all steps of the methods described herein are computer implemented.

According to a further aspect, there is provided a method of providing a prognosis for a subject that has been diagnosed as having cancer, the method comprising identifying a plurality of tumour-specific mutations in one or more samples from the subject and determining the likelihood of each of the tumour-specific mutations being clonal using the method of any embodiment of the first aspect.

The method may further comprise classifying the subject as having high clonal neoantigen burden vs low clonal neoantigen burden depending at least in part on the proportion of tumour-specific mutations that have a probability of being clonal above a predetermined threshold, wherein subjects with high clonal neoantigen burden have an improved prognosis compared to subjects with a low clonal neoantigen burden.

According to a further aspect, there is provided a method of providing an immunotherapy for a subject that has been diagnosed as having cancer, the method comprising: identifying one or more clonal neoantigens using a method as described herein, such as a method according to any embodiment of the second aspect; and designing an immunotherapy that targets one or more of the clonal neoantigens identified.

The method may have any one or more of the following features.

The immunotherapy that targets the one or more of the clonal neoantigens may be an immunogenic composition, a composition comprising immune cells or a therapeutic antibody. The immunogenic composition may comprise the one or more clonal of the clonal neoantigens identified (such as e.g. a neoantigen peptide or protein or a cell displaying the neoantigen), or material sufficient for expression of the one or more of the clonal neoantigens identified (e.g. a DNA or RNA molecule which encodes the neoantigen). The composition comprising immune cells may comprise T cells, B cells and/or dendritic cells. The composition comprising a therapeutic antibody may comprise one or more antibodies that recognise at least one of the one or more of the clonal neoantigens identified. An antibody may be a monoclonal antibody.

In any embodiment of any aspect, the cancer may be selected from bladder cancer, gastric cancer, oesophageal cancer, breast cancer, colorectal cancer, cervical cancer, ovarian cancer, endometrial cancer, kidney cancer (renal cell), lung cancer (small cell, non-small cell and mesothelioma), brain cancer (gliomas, astrocytomas, glioblastomas), melanoma, lymphoma, small bowel cancers (duodenal and jejunal), leukemia, pancreatic cancer, hepatobiliary tumours, germ cell cancers, prostate cancer, head and neck cancers, thyroid cancer and sarcomas. The cancer may be lung cancer. The cancer may be melanoma. The cancer may be bladder cancer. The cancer may be head and neck cancer.

In any embodiment of any aspect, the subject may be human.

Designing an immunotherapy that targets one or more of the clonal neoantigens identified may comprise designing one or more candidate peptides for each of the one or more clonal neoantigens targeted, each peptide comprising at least a portion of a clonal neoantigen targeted.

The method may further comprise obtaining the one or more candidate peptides. The method may further comprise testing the one or more candidate peptides for one or more properties. Testing may be performed in vitro or in silico. For example, the one or more peptides may be tested for immunogenicity, propensity to be displayed by MHC molecules (optionally by specific MHC molecule alleles, where the alleles may have been chosen depending on the MHC alleles expressed by the subject), ability to elicit proliferation of a population of immune cells, etc.

The method may further comprise producing the immunotherapy. The method may further comprise obtaining a population of dendritic cells that has been pulsed with one or more of the candidate peptides. The immunotherapy may be a composition comprising T cells that recognise at least one of the one or more of the clonal neoantigens identified. The composition may be enriched for T cells that target at least one of the one or more of the clonal neoantigens identified. The method may comprise obtaining a population of T cells and expanding the population of T cells to increase the number or relative proportion of T cells that target at least one of the one or more of the clonal neoantigens identified.

The method may further comprise obtaining a T cell population. A T cell population may be isolated from the subject, for example from one or more tumour samples obtained from the subject, or from a peripheral blood sample or a sample from other tissues of the subject. The T cell population may comprise tumour infiltrating lymphocytes. T cells may be isolated using methods which are well known in the art. For example, T cells may be purified from single cell suspensions generated from samples on the basis of expression of CD3, CD4 or CD8. T cells may be enriched from samples by passage through a Ficoll-paque gradient.

The method may further comprise expanding the T cell population. For example, T cells may be expanded by ex vivo culture in conditions which are known to provide mitogenic stimuli for T cells. By way of example, the T cells may be cultured with cytokines such as IL-2 or with mitogenic antibodies such as anti-CD3 and/or CD28. The T cells may be co-cultured with antigen-presenting cells (APCs), which may have been irradiated. The APCs may be dendritic cells or B cells. The dendritic cells may have been pulsed with peptides containing one or more of the identified neoantigens as single stimulants or as pools of stimulating neoantigen peptides. Expansion of T cells may be performed using methods which are known in the art, including for example the use of artificial antigen presenting cells (aAPCs), which provide additional co-stimulatory signals, and autologous PBMCs which present appropriate peptides. Autologous PBMCs may be pulsed with peptides containing neoantigens as discussed herein as single stimulants, or alternatively as pools of stimulating neoantigens.

According to a further aspect, there is provided a method for expanding a T cell population for use in the treatment of cancer in a subject, the method comprising: identifying one or more clonal neoantigens using a method as described herein, such as a method according to any embodiment of the second aspect; obtaining a T cell population comprising a T cell which is capable of specifically recognising one of the identified clonal neoantigens; and co-culturing the T cell population with a composition comprising the identified clonal neoantigens.

The method may have one or more of the following features.

The T cell population obtained may be assumed to comprise a T cell capable of specifically recognising one of the identified clonal neoantigens. The method preferably comprises identifying a plurality of clonal neoantigens. The T cell population may comprise a plurality of T cells each of which is capable of specifically recognising one of the plurality of identified clonal neoantigens, and co-culturing the T cell population with a composition comprising the plurality of identified clonal neoantigens. The co-culture may result in expansion of the T cell population that specifically recognises the one or more neoantigens. The expansion may be performed by co-culture of a T cell with a neoantigen and an antigen presenting cell. The antigen presenting cell may be a dendritic cell. Thus, the expansion may be a selective expansion of T cells which are specific for the neoantigen. The expansion may further comprise one or more non-selective expansion steps.

According to a further aspect, there is provided a composition comprising a population of T cells obtained or obtainable by a method according to any embodiment of the preceding aspect.

According to a further aspect, there is provided a composition comprising a neoantigen, neoantigen specific immune cell, or an antibody that recognises a neoantigen, for use in the treatment or prevention of cancer in a subject, wherein said neoantigen has been identified as a clonal neoantigen using the methods described herein.

According to a further aspect, there is provided a composition comprising a neoantigen, neoantigen specific immune cell, or an antibody that recognises a neoantigen, wherein said neoantigen has been identified as a clonal neoantigen using the methods described herein.

According to a further aspect, there is provided a cell or population of cells expressing a neoantigen on its surface, wherein said neoantigen has been identified as a clonal neoantigen using the methods described herein.

According to a further aspect, there is provided a neoantigen, immune cell which recognises a neoantigen, or antibody which recognises a neoantigen, for use in the treatment or prevention of cancer in a subject, wherein said neoantigen has been identified as a clonal neoantigen using the methods described herein.

According to a further aspect, there is provided a use of a neoantigen, immune cell which recognises a neoantigen, or antibody which recognises a neoantigen, in the manufacture of a medicament for use in the treatment or prevention of cancer in a subject, wherein said neoantigen has been identified as a clonal neoantigen using the methods described herein.

According to a further aspect, there is provided a method of treating a subject that has been diagnosed as having cancer, the method comprising administering an immunotherapy that has been provided using the methods described herein, or a composition as described herein.

According to a further aspect, there is provided a system comprising: a processor; and a computer readable medium comprising instructions that, when executed by the processor, cause the processor to perform the steps of any method described herein, such as a method according to any embodiment of the first, second, third or fourth aspects above.

According to a further aspect, there is provided or more non-transitory computer readable media comprising instructions that, when executed by one or more processors, cause the one or more processors to perform the steps of any method described herein, such as a method according to any embodiment of the first, second, third or fourth aspects above.

According to a further aspect, there is provided a computer program comprising code which, when the code is executed on a computer, causes the computer to perform the steps of any method described herein, such as a method according to any embodiment of the first, second, third or fourth aspects above.

DETAILED DESCRIPTION

Figure 1:
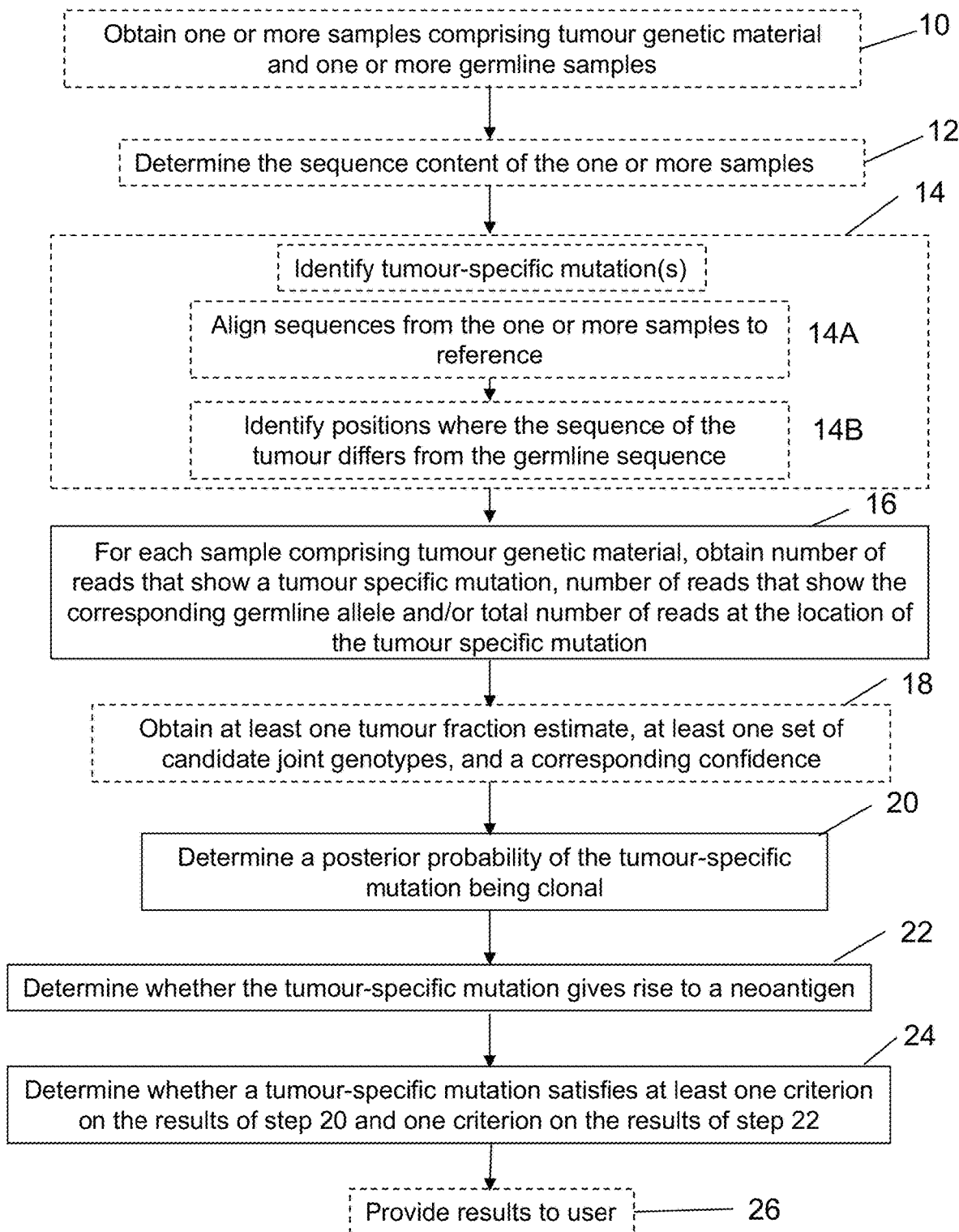
FIG. 1 is a flowchart illustrating schematically a method of determining whether a tumour-specific mutation is likely to be clonal, and its use in identifying clonal neoantigens.

Considering their importance in cancer therapy and prognosis, there is clear clinical applications for methods to identify clonal mutations and neoantigens in cancer patients. Multiple methods have been proposed to attempt to reconstruct the clonal architecture of tumour samples (Schwartz and Schaeffer, 2017). However, all of these approaches have various drawbacks that limit their clinical utility. Thus, the inventors have identified that there is still a need for improved methods for determining whether a tumour-specific mutation is likely to be clonal. This problem of identifying clonal mutations (mutations present in all cells of the cancer) in cancer is far from trivial. Indeed, primary samples contain a mixture of cells (including normal and cancer cells), and cancer genomes often contain extensive and heterogeneous copy number variations. Thus, the allelic prevalence of a mutation is the result of a combination of factors including the proportion of normal cells, the proportion of tumour cells that have the mutation, and the number of allelic copies of the mutation in each of these tumour cells. This is further compounded by sources of technical noise associated with any experimental protocol (e.g. sequencing errors), limitations of those protocols (e.g. short read alignment uncertainty), and the inherent limitation that a primary sample represents a partial snapshot of the state of a cancer. Roth et al. (2014) attempted to tackle this challenge by proposing a Bayesian clustering method (called "PyClone") for grouping sets of deeply sequenced somatic mutations into clusters that share the same evolutionary history. This is done by estimating their cellular prevalence and accounting for allelic imbalances introduced by segmental copy-number changes and normal cell contamination.

While this approach is advantageously underlined by a clear statistical framework, the present inventors identified that it is poorly suited to use in non-research environments for a plurality of reasons. Firstly, the approach is relatively slow, and operates at the level of sets of mutations (such as large sets of deeply sequenced mutations, or more recently, complete genomes) rather than individual mutations. Both of these drawbacks are a consequence of the fact that this method infers a clustering structure over the entire set of mutations. As such, the approach solves a complex problem requiring the calculation of posterior densities for model parameters including the cellular prevalence for each mutation in the set of all mutations identified in a plurality of samples from a cancer, as well as the clustering structure over this set of mutations. The inventors have identified that this was undesirable for at least two reasons: the approach is unnecessarily slow if the clustering structure over the entire set of mutations is not of interest, and the approach prevents traceability of any mutation through a clinical pipeline independently of other mutations analysed at the same time.

Indeed, identification of any mutation as likely to be clonal is inherently linked to the other mutations that were analysed together. Thus, any change in the set of mutations to be analysed requires re-running of the pipeline and potentially produces a different result. By contrast, the approach proposed by the inventors analyses each mutation independently, and does not infer any structure that depends on a population of mutations. This provides a clear improvement to computer technology because the computational complexity of the algorithm developed by the inventors is lower than that of the conventional technique (PyClone), thus the computational resources (processor, memory and/or network resources) required are lower overall and for each mutation. Further, the processing for a set of mutations is fully parallelisable as there is no dependency between mutations. This results in a further decrease in complexity, increase in processing speed, and improved tractability as any problem in a run for a single mutation does not impact the runs for other mutations.

Additionally, the prior art approach requires expert manual intervention to translate the output into an indication of clonality, by analysing the clustering structure and choosing a cluster of mutations assumed to be clonal, as well as prioritising mutations within the chosen cluster. Finally, the approach also requires expert manual intervention to choose appropriate copy number estimates as wrong copy number solutions greatly affect the clustering results, and approaches to set copy numbers automatically with the required level of reliability are lacking. These multiple levels of manual interventions are problematic not only because they require the presence of a (human) expert for a work that would be more efficiently done by a machine. Indeed, the process that is applied by an expert in selecting a copy number solution, choosing a cluster of mutations assumed to be clonal and prioritising mutations within this cluster simply cannot be reliably automated. The process requires expert knowledge and relies on an expert using their judgement to make choices that are ultimately subjective at least to some extent. This cannot be automated and also cannot be reliably reproduced as the process involves subjectivity. By contrast, according to the method of the present invention, none of these manual interventions are necessary. Multiple copy number solutions and their confidence can be seamlessly integrated (such that none needs to be chosen either manually or automatically), and a likelihood of clonality is predicted for each mutation individually (such that no choice of a cluster of mutations or prioritisation within this cluster is necessary, and a natural, predictable and reproducible order of prioritisation can be defined based on the predicted likelihoods). Thus, clonal mutations are identified more reliably than was previously possible, enabling their use beyond pure research and into the field of therapeutics development. The availability of reliable estimates of likelihood of clonality for individual mutations represents a clear improvement to the field of cancer therapeutics, and cancer monitoring and management, as although the potential use of such clonal mutations in these fields was postulated, the lack of tools to reliably identify these mutations for integration in a clinical pipeline hindered their actual use in practice.

In the present disclosure, the following terms will be employed, and are intended to be defined as indicated below.

A "sample" as used herein may be a cell or tissue sample, a biological fluid, an extract (e.g. a DNA extract obtained from the subject), from which genomic material can be obtained for genomic analysis, such as genomic sequencing (e.g. whole genome sequencing, whole exome sequencing). The sample may be a cell, tissue or biological fluid sample obtained from a subject (e.g. a biopsy). Such samples may be referred to as "subject samples". In particular, the sample may be a blood sample, or a tumour sample, or a sample derived therefrom. The sample may be one which has been freshly obtained from a subject or may be one which has been processed and/or stored prior to genomic analysis (e.g. frozen, fixed or subjected to one or more purification, enrichment or extraction steps). The sample may be a cell or tissue culture sample. As such, a sample as described herein may refer to any type of sample comprising cells or genomic material derived therefrom, whether from a biological sample obtained from a subject, or from a sample obtained from e.g. a cell line. In embodiments, the sample is a sample obtained from a subject, such as a human subject. The sample is preferably from a mammalian (such as e.g. a mammalian cell sample or a sample from a mammalian subject, such as a cat, dog, horse, donkey, sheep, pig, goat, cow, mouse, rat, rabbit or guinea pig), preferably from a human (such as e.g. a human cell sample or a sample from a human subject). Further, the sample may be transported and/or stored, and collection may take place at a location remote from the genomic sequence data acquisition (e.g. sequencing) location, and/or any computer-implemented method steps described herein may take place at a location remote from the sample collection location and/or remote from the genomic data acquisition (e.g. sequencing) location (e.g. the computer-implemented method steps may be performed by means of a networked computer, such as by means of a "cloud" provider).

A "mixed sample" refers to a sample that is assumed to comprise multiple cell types or genetic material derived from multiple cell types. Within the context of the present disclosure, a mixed sample is typically one that comprises tumour cells, or is assumed (expected) to comprise tumour cells, or genetic material derived from tumour cells. Samples obtained from subjects, such as e.g. tumour samples, are typically mixed samples (unless they are subject to one or more purification and/or separation steps). Typically, the sample comprises tumour cells and at least one other cell type (and/or genetic material derived therefrom). For example, the mixed sample may be a tumour sample. A "tumour sample" refers to a sample derived from or obtained from a tumour. Such samples may comprise tumour cells and normal (non-tumour) cells. The normal cells may comprise immune cells (such as e.g. lymphocytes), and/or other normal (non-tumour) cells. The lymphocytes in such mixed samples may be referred to as "tumour-infiltrating lymphocytes" (TIL). A tumour may be a solid tumour or a non-solid or haematological tumour. A tumour sample may be a primary tumour sample, tumour-associated lymph node sample, or a sample from a metastatic site from the subject. A sample comprising tumour cells or genetic material derived from tumour cells may be a bodily fluid sample. Thus, the genetic material derived from tumour cells may be circulating tumour DNA or tumour DNA in exosomes. Instead or in addition to this, the sample may comprise circulating tumour cells. A mixed sample may be a sample of cells, tissue or bodily fluid that has been processed to extract genetic material. Methods for extracting genetic material from biological samples are known in the art. A mixed sample may have been subject to one or more processing steps that may modify the proportion of the multiple cell types or genetic material derived from the multiple cell types in the sample. For example, a mixed sample comprising tumour cells may have been processed to enrich the sample in tumour cells. Thus, a sample of purified tumour cells may be referred to as a "mixed sample" on the basis that small amounts of other types of cells may be present, even if the sample may be assumed, for a particular purpose, to be pure (i.e. to have a tumour fraction of 1 or 100%).

The term "tumour fraction" (also sometimes referred to as "tumour purity" or simply "purity", or aberrant cell fraction (ACF)) refers to the proportion of DNA containing cells within a mixed sample that are tumour cells, or to the equivalent proportion that is assumed to result in a particular mixture of genetic material from tumour and non-tumour cells in a sample. Methods for determining the tumour fraction in a sample are known in the art. For example, in the context of cell or tissue samples, a tumour fraction may be estimated by analysing pathology slides (e.g. hematoxylin and eosin (H&E)-stained slides or other histochemistry or immunohistochemistry slides , by counting tumour cells in one or more representative areas of a sample), or using high throughput assays such as flow cytometry. In the context of samples comprising genetic material, a tumour fraction may be estimated using sequence analysis processes that attempt to deconvolute tumour and germline genomes such as e.g. ASCAT (Van Loo et al., 2010), ABSOLUTE (Carter et al., 2012), or ichorCNA (Adalsteinsson et al., 2017).

A "normal sample" or "germline sample" refers to a sample that is assumed not to comprise tumour cells or genetic material derived from tumour cells. A germline sample may be a blood sample, a tissue sample, or a purified sample such as a sample of peripheral blood mononuclear cells from a subject. Similarly, the terms "normal", "germline" or "wild type" when referring to sequences or genotypes refer to the sequence/genotype of cells other than tumour cells. A germline sample may comprise a small proportion of tumour cells or genetic material derived therefrom, and may nevertheless be assumed, for practical purposes, not to comprise said cells or genetic material. In other words, all cells or genetic material may be assumed to be normal and/or sequence data that is not compatible with the assumption may be ignored.

The term "sequence data" refers to information that is indicative of the presence and preferably also the amount of genomic material in a sample that has a particular sequence. Such information may be obtained using sequencing technologies, such as e.g. next generation sequencing (NGS), for example whole exome sequencing (WES), whole genome sequencing (WGS), or sequencing of captured genomic loci (targeted or panel sequencing), or using array technologies, such as e.g. copy number variation arrays, or other molecular counting assays. When NGS technologies are used, the sequence data may comprise a count of the number of sequencing reads that have a particular sequence. When non-digital technologies are used such as array technology, the sequence data may comprise a signal (e.g. an intensity value) that is indicative of the number of sequences in the sample that have a particular sequence, for example by comparison to an appropriate control. Sequence data may be mapped to a reference sequence, for example a reference genome, using methods known in the art (such as e.g. Bowtie (Langmead et al., 2009)). Thus, counts of sequencing reads or equivalent nondigital signals may be associated with a particular genomic location (where the "genomic location" refers to a location in the reference genome to which the sequence data was mapped). Further, a genomic location may contain a mutation, in which case counts of sequencing reads or equivalent non-digital signals may be associated with each of the possible variants (also referred to as "alleles") at the particular genomic location. The process of identifying the presence of a mutation at a particular location in a sample is referred to as "variant calling" and can be performed using methods known in the art (such as e.g. the GATK HaplotypeCaller, gatk.broadinstitute.org/hc/en-us/articles/360037225632-HaplotypeCaller). For example, sequence data may comprise a count of the number of reads (or an equivalent non-digital signal) which match a germline (also sometimes referred to as "reference") allele at a particular genomic location, and a count of the number of reads (or an equivalent non-digital signal) which match a mutated (also sometimes referred to as "alternate") allele at the genomic location.

Further, sequence data may be used to infer copy number profiles along a genome, using methods known in the art. Copy number profiles may be allele specific. In the context of the present disclosure, copy number profiles are preferably allele specific and tumour/normal sample specific. In other words, the copy number profiles used in the present disclosure are preferably obtained using methods designed to analyse samples comprising a mixture of tumour and normal cells, and to produce allele-specific copy number profiles for the tumour cells and the normal cells in a sample. Allele specific copy number profiles for mixed samples may be obtained from sequence data (e.g. using read counts as described above), using e.g. ASCAT (Van Loo et al., 2010). Other methods are known and equally suitable. Preferably, within the context of the present disclosure, the method used to obtain allele-specific copy number profiles is one that reports a plurality of possible copy number solutions and an associated quality/confidence metric. For example, ASCAT outputs a goodness-of-fit metric for each combination of values of ploidy (ploidy for a whole tumour sample, not segment-specific) and purity for which a corresponding allele-specific copy number profile was evaluated. Note that the tumour-specific copy number profiles generated by such methods represent an average or summary of the entire tumour cell population (i.e. it does not account for heterogeneity within the tumour population, which is the object of the new developments described herein).

The term "total copy number" refers to the total number of copies of a genomic region in a sample. The term "major copy number" refers to the number of copies of the most prevalent allele in a sample. Conversely, the term "minor copy number" refers to the number of copies of the allele other than the most prevalent allele in a sample. Unless indicated otherwise, these terms refer to the inferred major and major copy numbers (and total copy numbers) for an inferred tumour copy number profile. The term "normal copy number" or "normal total copy number" refers to the number of copies of a genomic region in the normal cells in a sample. Normal cells typically have two copies of each chromosome (unless the cell is genetically male and the chromosome is a sex chromosome), and hence the normal copy number may in embodiments be assumed to be equal to 2 (unless the genomic region is on the X or Y chromosome and the sample under analysis is from a male subject, in which case the normal copy number may be assumed to be equal to 1). Alternatively, the normal copy number for a particular genomic region may be determined using a normal sample.

The term "log R value" (sometimes referred to as "log R", "log RR", "LLR") refers to a measure of normalised total signal intensity, quantifying the total copy number at a genomic locus. In the context of the present disclosure, the term typically refers to the log R value for a sample comprising tumour genetic material, and the normalisation is typically performed by reference to a normal sample (which is preferably a matched normal sample but may also be a process-matched normal sample or other suitable normal reference sample). For example, where NGS is used, the logR may be obtained as the normalised log transform of read depth (log(read depth tumour/read depth normal)). The term "mean B allele frequency" (MBAF, also sometimes referred to as "B allele frequency" (BAF)) is a measure of normalised allelic intensity ratio at a genomic location. In the context of the present disclosure, the term typically refers to the BAF value for a sample comprising tumour genetic material, and the normalisation is typically performed by reference to a normal sample (which is preferably a matched normal sample but may also be a process-matched normal sample or other suitable normal reference sample). For example, the BAF may be obtained as the ratio of the allele frequency for the tumour allele vs the normal allele. Copy number profiles typically comprise copy number estimates over genomic regions called "segments". Thus, the BAF and logR associated with a genomic location may refer to the BAF and logR of the segment overlapping a particular genomic location (such as e.g. the genomic location of a mutation). Further, the BAF and logR can be used to obtain corresponding major and minor copy numbers. In embodiments, the values of copy number metrics may be provided for both a tumour copy number profile estimate and a normal copy number profile estimate, even if only the tumour copy number profile values are used.

The terms "tumour-specific mutation", "somatic mutation" or simply "mutation" are used interchangeably and refer to a difference in a nucleotide sequence (e.g. DNA or RNA) in a tumour cell compared to a healthy cell from the same subject. The difference in the nucleotide sequence can result in the expression of a protein which is not expressed by a healthy cell from the same subject. For example, a mutation may be a single nucleotide variant (SNV), multiple nucleotide variant (MNV), a deletion mutation, an insertion mutation, a translocation, a missense mutation, a translocation, a fusion, a splice site mutation, or any other change in the genetic material of a tumour cell. A mutation may result in the expression of a protein or peptide that is not present in a healthy cell from the same subject. Mutations may be identified by exome sequencing, RNA-sequencing, whole genome sequencing and/or targeted gene panel sequencing and or routine Sanger sequencing of single genes, followed by sequence alignment and comparing the DNA and/or RNA sequence from a tumour sample to DNA and/or RNA from a reference sample or reference sequence (e.g. the germline DNA and/or RNA sequence, or a reference sequence from a database). Suitable methods are known in the art.

An "indel mutation" refers to an insertion and/or deletion of bases in a nucleotide sequence (e.g. DNA or RNA) of an organism. Typically, the indel mutation occurs in the DNA, preferably the genomic DNA, of an organism. In embodiments, the indel may be from 1 to 100 bases, for example 1 to 90, 1 to 50, 1 to 23 or 1 to 10 bases. An indel mutation may be a frameshift indel mutation. A frameshift indel mutation is a change in the reading frame of the nucleotide sequence caused by an insertion or deletion of one or more nucleotides. Such frameshift indel mutations may generate a novel open-reading frame which is typically highly distinct from the polypeptide encoded by the non-mutated DNA/RNA in a corresponding healthy cell in the subject.

A "neoantigen" (or "neo-antigen") is an antigen that arises as a consequence of a mutation within a cancer cell. Thus, a neoantigen is not expressed (or expressed at a significantly lower level) by normal (i.e. non-tumour) cells. A neoantigen may be processed to generate distinct peptides which can be recognised by T cells when presented in the context of MHC molecules. As described herein, neoantigens may be used as the basis for cancer immunotherapies. References herein to "neoantigens" are intended to include also peptides derived from neoantigens. The term "neoantigen" as used herein is intended to encompass any part of a neoantigen that is immunogenic. An "antigenic" molecule as referred to herein is a molecule which itself, or a part thereof, is capable of stimulating an immune response, when presented to the immune system or immune cells in an appropriate manner. The binding of a neoantigen to a particular MHC molecule (encoded by a particular HLA allele) may be predicted using methods which are known in the art. Examples of methods for predicting MHC binding include those described by Lundegaard et al., O'Donnel et al., and Bullik-Sullivan et al. For example, MHC binding of neoantigens may be predicted using the netMHC-3 (Lundegaard et al.) and netMHCpan4 (Jurtz et al.) algorithms. A neoantigen that has been predicted to bind to a particular MHC molecule is thereby predicted to be presented by said MHC molecule on the cell surface.

A "clonal neoantigen" (also sometimes referred to as "truncal neoantigen") is a neoantigen that results from a mutation that is present in essentially every tumour cell in one or more samples from a subject (or that can be assumed to be present in essentially every tumour cell from which the tumour genetic material in the sample(s) is derived). Similarly, a "clonal mutation" (sometimes referred to as "truncal mutation") is a mutation that is present in essentially every tumour cell in one or more samples from a subject (or that can be assumed to be present in essentially every tumour cell from which the tumour genetic material in the sample(s) is derived). Thus, a clonal mutation may be a mutation that is present in every tumour cell in one or more samples from a subject. A "sub-clonal" neoantigen is a neoantigen that results from a mutation that is present in a subset or a proportion of cells in one or more tumour samples from a subject (or that can be assumed to be present in a subset of the tumour cells from which the tumour genetic material in the sample(s) is derived). Similarly, a "sub-clonal" mutation is a mutation that is present in a subset or a proportion of cells in one or more tumour samples from a subject (or that can be assumed to be present in a subset of the tumour cells from which the tumour genetic material in the sample(s) is derived). A neoantigen or mutation may be clonal in the context of one or more samples from a subject while not being truly clonal in the context of the entirety of the population of tumour cells that may be present in a subject (e.g. including all regions of a primary tumour and metastasis). Thus, a clonal mutation may be "truly clonal" in the sense that it is a mutation that is present in essentially every tumour cell (i.e. in all tumour cells) in the subject. This is because the one or more samples may not be representative of each and every subset of cells present in the subject. Thus, within the context of the present disclosure, a "clonal neoantigen" or "clonal mutation" may also be referred to as a "ubiquitous neoantigen" or "ubiquitous mutation", to indicate that the neoantigen is present in essentially all tumour cells that have been analysed, but may not be present in all tumour cells that may exist in the subject. The terms "clonal" and "ubiquitous" are used interchangeably unless context indicates that reference to "true clonality" was intended. The wording "essentially every tumour cell" in relation to one or more samples or a subject may refer to at least 70%, at least 75%, at least 80%, at least 85%, at least 90%, at least 91%, at least 92%, at least 93%, at least 94% at least 95%, at least 96%, at least 97%, at least 98%, or at least 99% of the tumour cells in the one or more samples or the subject.

Nevertheless, a neoantigen/mutation that is identified as likely to be clonal (or "ubiquitous") as described herein is likely to be truly clonal, or at least more likely to be truly clonal than a neoantigen/mutation that is identified as unlikely to be clonal. Further, the confidence in the likelihood that a clonal neoantigen/mutation identified herein is truly clonal increases when the sample(s) used to identify the clonal neoantigen/mutation capture a more complete picture of the genetic diversity of the tumour (e.g. by including a plurality of samples from the subject, such as e.g. samples from different regions of the tumour, and/or by including samples that inherently capture a diversity of tumour cells such as e.g. ctDNA samples). Conversely, a neoantigen/mutation that is identified as unlikely to be clonal as described herein is unlikely to be truly clonal, because the identification that the neoantigen/mutation is unlikely to be clonal indicates that even in the restricted view afforded by the sampling process, there is evidence that the neoantigen/mutation is not present in all tumour cells. Thus, the process of identifying clonal neoantigens/mutations may be seen as prioritising which candidate neoantigens/mutations are most likely to be clonal, based on the restricted view of the clonal structure of the subject's tumour available from the one or more samples.

The term "cancer cell fraction" (or "CCF") refers to the proportion of tumour cells that contain a mutation, such as e.g. a mutation that results in a particular neoantigen. Within the context of the present disclosure, the cancer cell fraction may be estimated based on one or more samples, and as such may not be equal to the true cancer cell fraction in the subject (as explained above). Nevertheless, the cancer cell fraction estimated based on one or more samples may provide a useful indication of the likely true cancer cell fraction. Further, as explained above, the accuracy of such an estimate may increase when the sample(s) used to estimate the cancer cell fraction capture a more complete picture of the genetic diversity of the tumour. Additional sources of noise and confounding factors in genomic data mean that a cancer cell fraction determined from one or more samples represents an estimate. As such, although a truly clonal mutation/neoantigen should have a CCF=1, in practice mutations/neoantigens that are more likely to be clonal are expected to be associated with a higher CCF estimate (which may not be equal to 1) than mutations that are less likely to be clonal, which are expected to be associated with a lower CCF estimate.

For example, a cancer cell fraction estimate may be obtained by integrating variant allele frequencies with copy numbers and purity estimates as described by Landau et al. (2013). Such a CCF estimate can also be used to identify mutations that are likely to be clonal. For example, a clonal mutation may be defined as a mutation which has an estimated cancer cell fraction (CCF)≥0.75, such as a CCF≥0.80, 0.85. 0.90, 0.95 or 1.0. A subclonal mutation may be defined as a mutation which has a CCF<0.95, 0.90, 0.85, 0.80, or 0.75. Further, a CCF estimate may be associated with (e.g. derived from) a distribution associating a probability with each of a plurality of possible values of CCF between 0 and 1, from which statistical estimates of confidence may be obtained. For example, a mutation may be defined as likely to be a clonal mutation if the 95% CCF confidence interval is >=0.75, i.e. the upper bound of the 95% confidence interval of the estimated CCF is greater than or equal to 0.75. In other words, a mutation may be defined as likely to be a clonal mutation if there is an interval of CCF with lower bound L and upper bound H that is such that $P(L<CCF<H)=95\%$ with $H>=0.75$. Alternatively, a mutation may be identified as clonal if there is more than a 50% chance or probability that its cancer cell fraction (CCF) reaches or exceeds the required value as defined above, for example 0.75 or 0.95, such as a chance or probability of 50%, 55%, 60%, 65%, 70%, 75%, 80%, 85%, 90%, 95% or more. In other words, a mutation may be identified as clonal if $P(CCF>0.75)>=0.5$. For example, mutations may be classified as likely clonal or subclonal based on whether the posterior probability that their CCF exceeds 0.95 (or 0.75, or any other chosen threshold) is greater or lesser than 0.5, respectively.

According to the methods of the present disclosure, as will be described further below, a likelihood of a mutation being clonal is obtained. This is equivalent to $P(CCF=1)$. In this context, as will be explained further below, a mutation may be identified as likely to be clonal if $P(CCF=1)$ exceeds a threshold. The threshold may be fixed. For example, a mutation may be identified as likely to be clonal if $P(CCF=1)>0.05$. Alternatively, the threshold may be determined for a particular set of mutations that are investigated. In embodiments, the threshold may be set based on a benchmarking data set with known clonal/non-clonal status, to reach a predetermined precision and/or recall. A benchmarking data set may be obtained using synthetic data and/or using a data set obtained from a population with known clonality structure (for example a cell line mixture data). For example, a mutation may be identified as likely clonal if $P(CCF=1)>t$ where t is the maximum value that is such that 95% (or any other value such as e.g. 50%, 55%, 60%, 65%, 70%, 75%, 80%, 85%, 90%) of true clonal mutations in a benchmarking dataset are identified (i.e. a false negative rate of at most 5%). As another example, a mutation may be identified as likely clonal if $P(CCF=1)>t$ where t is the minimum value that is such that at least 50% (or any other value such as e.g. 50%, 55%, 60%, 65%, 70%, 75%, 80%, 85%, 90%) of the mutations that exceed the threshold in a benchmarking dataset are true clonal mutations (i.e. a true positive rate of at least 50%). Alternatively, the threshold may be set such that any mutation (or a certain % of mutations) that is associated with an estimated CCF that has a confidence interval meeting the criteria described above (e.g. it is such that the upper bound of the 95% confidence interval of the estimated CCF is greater than or equal to 0.75) is selected as likely to be clonal. Alternatively, the threshold may be set such that any mutation (or a certain % of mutations) that is associated with an estimated CCF that has a posterior probability distribution meeting the criteria described above (e.g. a posterior probability that their CCF exceeds 0.95 (or 0.75, or any other chosen threshold) is greater than 0.5) is selected as likely to be clonal.

A cancer immunotherapy (or simply "immunotherapy") refers to a therapeutic approach comprising administration of an immunogenic composition (e.g. a vaccine), a composition comprising immune cells, or an immunoactive drug, such as e.g. a therapeutic antibody, to a subject. The term "immunotherapy" may also refer to the therapeutic compositions themselves. In the context of the present disclosure, the immunotherapy typically targets a neoantigen. For example, an immunogenic composition or vaccine may comprise a neoantigen, neoantigen presenting cell or material necessary for the expression of the neoantigen. As another example, a composition comprising immune cells may comprise T and/or B cells that recognise a neoantigen.

The immune cells may be isolated from tumours or other tissues (including but not limited to lymph node, blood or ascites), expanded ex vivo or in vitro and re-administered to a subject (a process referred to as "adoptive cell therapy"). Instead or in addition to this, T cells can be isolated from a subject and engineered to target a neoantigen (e.g. by insertion of a chimeric antigen receptor that binds to the neoantigen) and re-administered to the subject. As another example, a therapeutic antibody may be an antibody which recognises a neoantigen. One skilled in the art will appreciate that if the neoantigen is a cell surface antigen, an antibody as referred to herein will recognise the neoantigen. Where the neoantigen is an intracellular antigen, the antibody will recognise the neoantigen peptide-MHC complex. As referred to herein, an antibody which "recognises" a neoantigen encompasses both of these possibilities. Further, an immunotherapy may target a plurality of neoantigens. For example, an immunogenic composition may comprise a plurality of neoantigens, cells presenting a plurality of neoantigens or the material necessary for the expression of the plurality of neoantigens. As another example, a composition may comprise immune cells that recognise a plurality of neoantigens. Similarly, a composition may comprise a plurality of immune cells that recognise the same neoantigen. As another example, a composition may comprise a plurality of therapeutic antibodies that recognise a plurality of neoantigens. Similarly, a composition may comprise a plurality of therapeutic antibodies that recognise the same neoantigen.

A composition as described herein may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

References to "an immune cell" are intended to encompass cells of the immune system, for example T cells, NK cells, NKT cells, B cells and dendritic cells. In a preferred embodiment, the immune cell is a T cell. An immune cell that recognises a neoantigen may be an engineered T cell. A neoantigen specific T cell may express a chimeric antigen receptor (CAR) or a T cell receptor (TCR) which specifically binds a neoantigen or a neoantigen peptide, or an affinity-enhanced T cell receptor (TCR) which specifically binds a neoantigen or a neoantigen peptide (as discussed further hereinbelow). For example, the T cell may express a chimeric antigen receptor (CAR) or a T cell receptor (TCR) which specifically binds to a neo-antigen or a neo-antigen peptide (for example an affinity enhanced T cell receptor (TCR) which specifically binds to a neo-antigen or a neo-antigen peptide). Alternatively, a population of immune cells that recognise a neoantigen may be a population of T cell isolated from a subject with a tumour. For example, the T cell population may be generated from T cells in a sample isolated from the subject, such as e.g. a tumour sample, a peripheral blood sample or a sample from other tissues of the subject. The T cell population may be generated from a sample from the tumour in which the neoantigen is identified. In other words, the T cell population may be isolated from a sample derived from the tumour of a patient to be treated, where the neoantigen was also identified from a sample from said tumour. The T cell population may comprise tumour infiltrating lymphocytes (TIL).

The term "Antibody" (Ab) includes monoclonal antibodies, polyclonal antibodies, multispecific antibodies (e.g., bispecific antibodies), and antibody fragments that exhibit the desired biological activity. The term "immunoglobulin" (Ig) may be used interchangeably with "antibody". Once a suitable neoantigen has been identified, for example by a method according to the disclosure, methods known in the art can be used to generate an antibody.

An "immunogenic composition" is a composition that is capable of inducing an immune response in a subject. The term is used interchangeably with the term "vaccine". The immunogenic composition or vaccine described herein may lead to generation of an immune response in the subject. An "immune response" which may be generated may be humoral and/or cell-mediated immunity, for example the stimulation of antibody production, or the stimulation of cytotoxic or killer cells, which may recognise and destroy (or otherwise eliminate) cells expressing antigens corresponding to the antigens in the vaccine on their surface. The immunogenic composition may comprise one or more neoantigens, or the material necessary for the expression of one or more neoantigens. In addition, a neoantigen may be delivered in the form of a cell, such as an antigen presenting cell, for example a dendritic cell. The antigen presenting cell such as a dendritic cell may be pulsed or loaded with the neo-antigen or neo-antigen peptide or genetically modified (via DNA or RNA transfer) to express one, two or more neo-antigens or neoantigen peptides, for example 2, 3, 4, 5, 6, 7, 8, 9 or 10 neo-antigens or neo-antigen peptides. Methods of preparing dendritic cell immunogenic compositions or vaccines are known in the art.

Neoantigen peptides may be synthesised using methods which are known in the art. The term "peptide" is used in the normal sense to mean a series of residues, typically L-amino acids, connected one to the other typically by peptide bonds between the a-amino and carboxyl groups of adjacent amino acids. The term includes modified peptides and synthetic peptide analogues. The neoantigen peptide may comprise the cancer cell specific mutation (e.g. the non-silent amino acid substitution encoded by a single nucleotide variant (SNV)) at any residue position within the peptide. By way of example, a peptide which is capable of binding to an MHC class I molecule is typically 7 to 13 amino acids in length. As such, the amino acid substitution may be present at position 1, 2, 3, 4, 5, 6, 7, 8, 9, 10, 11, 12 or 13 in a peptide comprising thirteen amino acids. In embodiments, longer peptides, for example 21-31-mers, may be used, and the mutation may be at any position, for example at the centre of the peptide, e.g. at positions 10, 11, 12, 13, 14, 15 or 16. Such peptides can also be used to stimulate both CD4 and CD8 cells to recognise neoantigens.

As used herein "treatment" refers to reducing, alleviating or eliminating one or more symptoms of the disease which is being treated, relative to the symptoms prior to treatment. "Prevention" (or prophylaxis) refers to delaying or preventing the onset of the symptoms of the disease. Prevention may be absolute (such that no disease occurs) or may be effective only in some individuals or for a limited amount of time.

As used herein, the terms "computer system" includes the hardware, software and data storage devices for embodying a system or carrying out a method according to the above described embodiments. For example, a computer system may comprise a central processing unit (CPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other non-transitory computer readable media. The computer system may include a plurality of computing devices connected by a network and able to communicate with each other over that network. It is explicitly envisaged that computer system may consist of or comprise a cloud computer.

As used herein, the term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

Identification of Clonal Mutations

The present disclosure provides methods for determining whether a tumour-specific mutation is likely to be clonal using sequence data from one or more samples comprising tumour cells or genetic material derived therefrom. The disclosure also provides methods for identifying clonal neoantigens comprising determining whether one or more tumour-specific mutations is/are likely to be clonal. An illustrative method will be described by reference to FIG. 1. At optional step 10, a sample comprising genomic material from a tumour may be obtained from a subject. The sample is typically a mixed sample comprising genomic material from multiple cell types including tumour cells. Preferably, a matched sample that does not comprise genomic material from tumour cells, or from which genomic material from normal cells can be extracted, may be obtained or may have been previously obtained. A matched sample is a sample obtained from the same subject as the tumour sample. The use of a matched normal sample improves the accuracy of calling of somatic (tumour-specific) mutations, as any variant position identified in the tumour sample can be compared to variant positions in the matched normal sample to exclude germline variants. The same matched normal sample may be used to analyse a plurality of tumour samples from a subject. Further, the matched sample and one or more tumour samples may have been obtained at different times. For example, a first tumour sample and matched sample may have been obtained at the time of diagnosis or resection of a tumour, and a further tumour sample may be obtained and analysed together with the initial matched sample at a later time point. When a matched sample is not available, a reference sample or genome including common somatic variants may be used. Alternatively, a processed matched normal sample may be used, which may not have been obtained from the same subject, or may have been obtained from a pool of subjects.

At optional step 12, the sequence content of the one or more mixed samples and optionally the matched sample may be determined, for example by sequencing the genomic material in the sample using one of whole exome sequencing, or whole genome sequencing. Alternative methods such as e.g. allele-specific copy number arrays may be used, although sequencing methods are preferred since they generate a digital output representative of the number of each particular sequence in a sample. At optional step 14, the sequence data may be analysed to identify one or more mutations that are likely to be present in the tumour cells but not in non-cancerous cells. These represent tumour-specific mutations and may be used as candidate neoantigens. This may comprise the steps of aligning the sequences from the one or more samples (i.e. the mixed sample(s) and the germline sample(s), if available), and identifying genomic locations where the sequence of the tumour differs from the germline sequence or can be assumed to differ from the germline sequence (e.g. if a germline sequence for the subject is not available).

At step 16, sequence data for the mixed sample at the genomic location of a candidate tumour-specific mutation is obtained, comprising the count of reads supporting the mutated allele (also referred to as "non-reference allele"), the count of reads supporting the germline allele(s) (A, collectively referred to as "germline allele" if the locus is heterozygous in the germline population, also referred to as "reference", "wild type" or "normal" allele) at the genomic location, and/or the total count of reads at the genomic location of the candidate tumour-specific mutation. Only two of these metrics need to be obtained as the third one can be deduced from any two of these. The sequence data may instead or in addition to this include read data or intensity data from which the counts can be obtained. At optional step 18, information about at least one copy number solution compatible with each sample comprising tumour-genetic material may be obtained. This information may comprise allele-specific copy number metrics for the tumour fraction of the sample selected from the major copy number, minor copy number, total copy number, mean B allele frequency, log R value and tumour ploidy, and the normal copy number, or information derived from these metrics such as a set of candidate joint genotypes that is compatible with these allele-specific copy number metrics. Not all such allele-specific copy number metrics are necessary as some contain redundant information and/or can be associated with suitable default values. For example, the normal copy number can be associated with a suitable default value as explained above. Further, only two of the major copy number, total copy number and minor copy number are necessary to infer the third one. Similarly, those three values can be inferred from the MBAF and logR values (and vice versa). Optionally, a copy number solution may be associated with a corresponding confidence metric. When such a metric is not available, each copy number solution may be assumed to be equally likely. Each candidate joint genotype comprises a genotype at the location of the tumour-specific mutation for a normal population, a reference tumour population that does not comprise the tumour-specific mutation and a variant tumour cell population that comprises the tumour-specific mutation.

At step 20, the probability of a tumour-specific mutation being clonal is determined as a posterior probability depending on: a prior probability of the mutation being clonal, and the probabilities of observing the sequence data if the tumour-specific mutation is (i) clonal and (ii) non-clonal, in view of a tumour fraction for each of the one or more samples and one or more candidate joint genotypes. A prior probability is a probability that represent a belief about a quantity before some evidence is taken into account. In the present context, a prior probability of a mutation being clonal may represent a probability of a mutation being clonal in the tumour, that is based on prior knowledge or assumptions, and does not take into account the sequence data from the mixed sample. At step 22, it is determined whether the tumour-specific mutation is likely to give rise to a neoantigen. For example, it may be determined whether the mutation is likely to result in a peptide or protein that is not expressed by a germline cell (whose genome does not contain the mutation). This step may be performed at any point after step 14, and in particular need not be performed after steps 16-20. For example, candidate tumour-specific mutations may be filtered depending on whether they are likely to give rise to a neoantigen prior to determining whether the tumour-specific mutation is likely to be clonal. At step 24, tumour-specific mutations that satisfy one or more criteria that apply to the results of step 20 and one or more criteria that apply to the results of step 22 may be identified. These may be considered to represent candidate clonal neoantigens. At optional step 26, the results of any of the preceding steps (and in particular steps 20 to 24) may be provided to a user, for example through a user interface. These results may be used for example to provide an immunotherapy or prognosis for a subject, as will be described further below.

Applications

The above methods find applications in the context of cancer diagnostic, prognostic and therapeutic approaches. In particular, the above methods may be used to provide immunotherapies that target clonal neoantigens. Thus, also described herein are methods of providing an immunotherapy for a subject, the method comprising identifying one or more clonal neoantigens from one or more samples from the subject.

Figure 2:
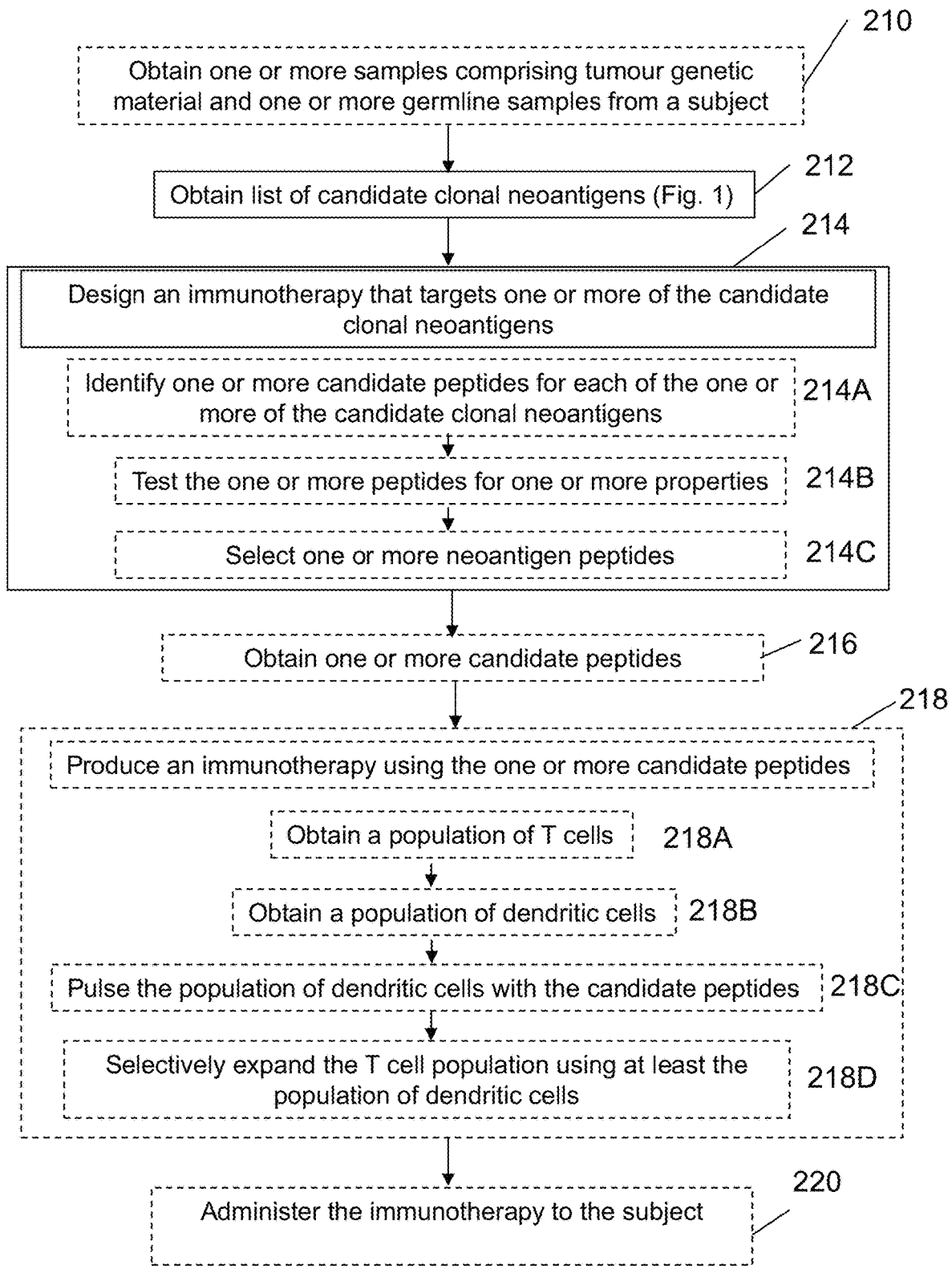
FIG. 2 is a flowchart illustrating schematically a method of providing an immunotherapy.

FIG. 2 illustrates schematically an exemplary method of providing an immunotherapy. At optional step 210, one or more samples comprising tumour genetic material and one or more germline samples are obtained from a subject. The subject may be a subject that has been diagnosed as having cancer, and may be (but does not need to be) the same subject for which the immunotherapy is provided. At step 212, a list of candidate clonal neoantigens is obtained using the methods described herein, for example by reference to FIG. 1. The list may comprise a single neoantigen, or a plurality of neoantigens. Preferably, the list comprises a plurality of neoantigens. At step 214, an immunotherapy that targets at least one (and optionally a plurality) of the candidate neoantigens is designed. Designing such an immunotherapy may comprise identifying one or more candidate peptides for each of the candidate clonal neoantigens (step 214A). For example, a plurality of peptides may be designed for at least one of the candidate clonal neoantigens, which differ in their lengths and/or the location of a sequence variation that characterises the neoantigen compared to the corresponding germline peptide. At step 214B, the one or more peptides identified may be tested in vitro and or in silico to evaluate one or more properties such as their immunogenicity, likelihood of being displayed by a MHC molecule, etc. At optional step 214C, one or more of the peptides may be selected, for example based on the results of step 214B.

At step 216, the selected peptides may be obtained. Peptides with selected sequences may be obtained using any method known in the art such as e.g. using an expression system or by direct synthesis. At step 218, an immunotherapy may be produced using the one or more candidate peptides. The immunotherapy may comprise the one or more candidate peptides or material sufficient for their expression (e.g. in the case of an immunogenic composition or vaccine), or may comprise molecules or cells that have been obtained using the candidate peptides (e.g. in the case of therapeutic antibodies that selectively bind the candidate peptides, or immune cells that specifically recognise the candidate peptides). At optional step 220, the immunotherapy may be administered to a subject, which is preferably the subject from which the samples used to identify the clonal neoantigens have been obtained. An example of producing an immunotherapy comprising a T cell population selectively enriched with T cells that recognise one or more clonal neoantigens will be described. At step 218A, a population of T cells may be obtained. The T cells may be obtained from the subject to be treated, but do not need to be. The T cells may be obtained from a tumour sample, from a blood sample, or from any other tissue sample. At step 218B, a population of dendritic cells may be obtained. For example, a population of dendritic cells may be derived from mononuclear cells (e.g. peripheral blood mononuclear cells, PBMCs) from the subject to be treated. At step 218C, the population of dendritic cells may be pulsed with the candidate peptides. At step 218D, the T cell population may be selectively expanded using the population of pulsed dendritic cells. Additional expansion factors such as e.g. cytokines or stimulating antibodies may be used.

Thus, the disclosure also provides a T cell composition comprising a T cell population selectively enriched with T cells that recognise one or more clonal neoantigens, wherein the one or more clonal neoantigens have been identified using any of the methods described herein.

In a T cell composition as described herein the expanded population of neoantigen-reactive T cells may have a higher activity than the population of T cells which have not been expanded, as measured by the response of the T cell population to restimulation with a neoantigen peptide. Activity may be measured by cytokine production, and wherein a higher activity is a 5-10 fold or greater increase in activity.

References to a plurality of clonal neoantigens may refer to a plurality of peptides or proteins each comprising a different tumour-specific mutation that gives rise to a neoantigen. Said plurality may be from 2 to 250, from 3 to 200, from 4 to 150, or from 5 to 100 tumour-specific mutations, for example from 5 to 75 or from 10 to 50 tumour-specific mutations. Each tumour-specific mutation may be represented by one or more clonal neoantigen peptides. In other words, a plurality of clonal neoantigens may comprise a plurality of different peptides, some of which comprise a sequence that includes the same tumour-specific mutation (for example at different positions within the sequence of the peptide, or within peptides of varying lengths).

A T cell population that is produced in accordance with the present disclosure will have an increased number or proportion of T cells that target one or more neoantigens that are predicted to be clonal. That is to say, the composition of the T cell population will differ from that of a "native" T cell population (i.e. a population that has not undergone the expansion steps discussed herein), in that the percentage or proportion of T cells that target a neoantigen that is predicted to be clonal will be increased. The T cell population according to the disclosure may have at least about 0.2, 0.3, 0.4, 0.5, 0 6, 0 7, 0 8, 0 9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100% T cells that target a neoantigen that is predicted to be clonal.

The immunotherapies described herein may be used in the treatment of cancer. Thus, the disclosure also provides a method of treating cancer in a subject comprising administering an immunotherapeutic composition as described herein to the subject.

Additionally, the presence of clonal neoantigens has been shown to be associated with improved prognosis in cancer. Thus, also described herein are methods of providing a prognosis for a subject that has been diagnosed as having a cancer, the method comprising determining the fraction and/or number of clonal neoantigens in one or more tumour samples from the subject.

Suitably, in any embodiment of any aspect described herein, the cancer may be ovarian cancer, breast cancer, endometrial cancer, kidney cancer (renal cell), lung cancer (small cell, non-small cell and mesothelioma), brain cancer (gliomas, astrocytomas, glioblastomas), melanoma, merkel cell carcinoma, clear cell renal cell carcinoma (ccRCC), lymphoma, small bowel cancers (duodenal and jejunal), leukemia, pancreatic cancer, hepatobiliary tumours, germ cell cancers, prostate cancer, head and neck cancers, thyroid cancer and sarcomas. For example, the cancer may be lung cancer, such as lung adenocarcinoma or lung squamous-cell carcinoma. As another example, the cancer may be melanoma. In embodiments, the cancer may be selected from melanoma, merkel cell carcinoma, renal cancer, non-small cell lung cancer (NSCLC), urothelial carcinoma of the bladder (BLAC) and head and neck squamous cell carcinoma (HNSC) and microsatellite instability (MSI)-high cancers. In some embodiments, the cancer is non-small cell lung cancer (NSCLC). In other embodiments, the cancer is melanoma.

Treatment using the compositions and methods of the present disclosure may also encompass targeting circulating tumour cells and/or metastases derived from the tumour. Treatment according to the present disclosure targeting one or more neoantigens may help prevent the evolution of therapy resistant tumour cells which may occur with standard approaches such as chemotherapy, radiotherapy, or non-specific immunotherapy. The methods and uses for treating cancer described herein may be performed in combination with additional cancer therapies. In particular, the T cell compositions described herein may be administered in combination with immune checkpoint intervention, co-stimulatory antibodies, chemotherapy and/or radiotherapy, targeted therapy or monoclonal antibody therapy. 'In combination' may refer to administration of the additional therapy before, at the same time as or after administration of the T cell composition as described herein.

The disclosure also provides a method for producing an immunotherapeutic composition, the method comprising identifying a neoantigen as likely to be clonal and producing an immunotherapeutic composition that targets the neoantigen.

Also described herein is a method of treating a subject that has been diagnosed as having cancer, the method comprising: identifying one or more clonal neoantigens by: identifying a plurality of tumour-specific mutations in the subject; determining whether one or more of the tumour-specific mutations is likely to be clonal in the subject; selecting one or more of the tumour-specific mutations as candidate clonal neoantigens, wherein a candidate clonal neoantigen is a tumour-specific mutation that satisfies at least one or more predetermined criteria on whether the tumour-specific mutation is likely to be clonal; and treating the subject with an immunotherapy that targets one or more of the selected candidate clonal neoantigens; wherein determining whether a tumour-specific mutation is likely to be clonal in a subject is performed using the methods described herein. In particular, determining whether a tumour-specific mutation is likely to be clonal in a subject may comprise: obtaining, by a processor, sequence data from one or more samples from the subject comprising tumour genetic material, the sequence data comprising for each of the one or more samples, at least two of: the number of reads in the sample that show the tumour-specific mutation ($d_b$), the number of reads in the sample that show the corresponding germline allele, and the total number of reads at the location of the tumour-specific mutation ($d$), and determining, by the processor, the likelihood that the tumour-specific mutation is clonal as a posterior probability depending on: a prior probability of the mutation being clonal, and the probabilities of observing the sequence data if the tumour-specific mutation is (i) clonal and (ii) non-clonal, in view of a tumour fraction for each of the one or more samples and one or more candidate joint genotypes each comprising a genotype at the location of the tumour-specific mutation for a normal population, a reference tumour population that does not comprise the tumour-specific mutation and a variant tumour cell population that comprises the tumour-specific mutation.

The candidate clonal neoantigens may be selected as tumour-specific mutations that further satisfy at least one or more predetermined criteria on whether the tumour-specific mutation is likely to give rise to a neoantigen. The step of selecting, by said processor, one or more of the tumour-specific mutations as candidate clonal neoantigens, may comprise determining whether the one or more tumour specific mutations satisfy one or more criteria on whether the tumour-specific mutation is likely to give rise to a neoantigen selected from: the mutation being associated with an expression product that is expressed in tumour cells, the mutation being predicted to result in a protein or peptide that is not expressed in the normal cells of the subject, the mutation being predicted to result in at least one peptide that is likely to be presented by an MHC molecule, the mutation being predicted to result in at least one peptide that is likely to be presented by an MHC allele that is known to be present in the subject, and the mutation being predicted to result in a protein or peptide that is immunogenic. The step of selecting, by said processor, one or more of the tumour-specific mutations as candidate clonal neoantigens, may comprise determining, by said processor, whether the one or more tumour specific mutations satisfy one or more predetermined criteria on whether the tumour-specific mutation is likely to be clonal selected from: the mutation having a likelihood of being clonal above a predetermined threshold, the mutation having a likelihood of being clonal that is above a threshold set adaptively to select a predetermined number of tumour-specific mutations with the highest likelihoods of being clonal amongst the tumour-specific mutations for which a likelihood was determined, and having a likelihood of being clonal that is above a threshold set adaptively to select a predetermined top percentile of tumour-specific mutations amongst the tumour-specific mutations for which a likelihood was determined.

The immunotherapy that targets the one or more of the selected clonal neoantigens may be an immunogenic composition, a composition comprising immune cells or a therapeutic antibody. The immunotherapy may be a composition comprising T cells that recognise at least one of the one or more of the selected clonal neoantigens identified. The composition may be enriched for T cells that target at least one of the one or more of the selected clonal neoantigens identified. The method may comprise obtaining a population of T cells and expanding the population of T cells to increase the number or relative proportion of T cells that target at least one of the one or more of the selected clonal neoantigens identified.

Systems

Figure 3:
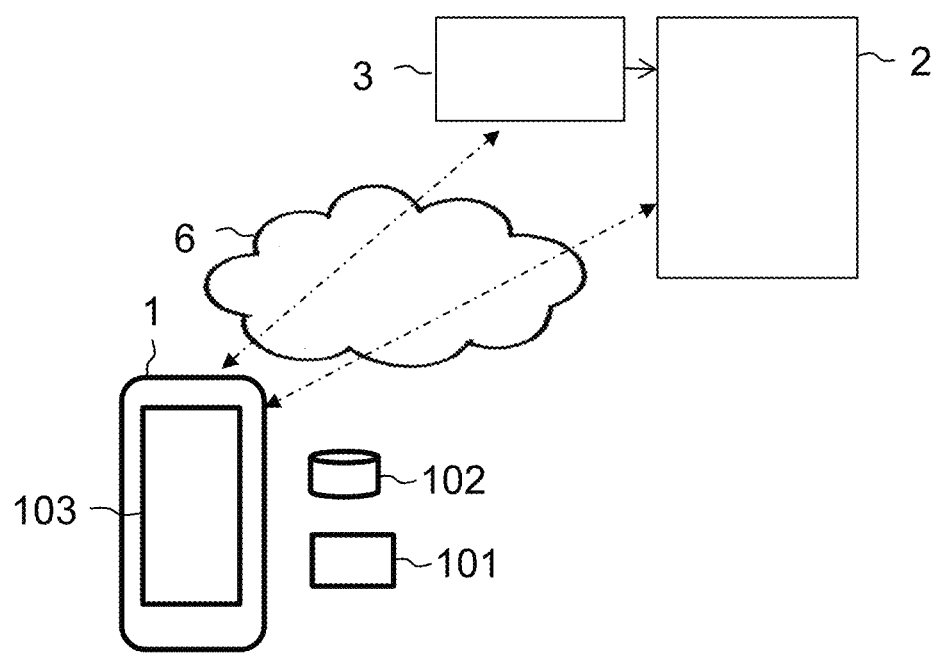
FIG. 3 shows an embodiment of a system for determining whether a tumour-specific mutation is likely to be clonal and/or for identifying clonal neoantigens and/or for providing an immunotherapy.

FIG. 3 shows an embodiment of a system for determining whether a tumour-specific mutation is likely to be clonal, and/or identifying clonal neoantigens and/or for providing a prognosis or providing an immunotherapy based at least in part on the identified clonal neoantigens, according to the present disclosure. The system comprises a computing device 1, which comprises a processor 101 and computer readable memory 102. In the embodiment shown, the computing device 1 also comprises a user interface 103, which is illustrated as a screen but may include any other means of conveying information to a user such as e.g. through audible or visual signals. The computing device 1 is communicably connected, such as e.g. through a network 6, to sequence data acquisition means 3, such as a sequencing machine, and/or to one or more databases 2 storing sequence data. The one or more databases may additionally store other types of information that may be used by the computing device 1, such as e.g. reference sequences, parameters, etc. The computing device may be a smartphone, tablet, personal computer or other computing device. The computing device is configured to implement a method for determining whether a tumour specific mutation is likely to be clonal, as described herein. In alternative embodiments, the computing device 1 is configured to communicate with a remote computing device (not shown), which is itself configured to implement a method of determining whether a tumour specific mutation is likely to be clonal, as described herein. In such cases, the remote computing device may also be configured to send the result of the method to the computing device. Communication between the computing device 1 and the remote computing device may be through a wired or wireless connection, and may occur over a local or public network such as e.g. over the public internet or over WiFi.

The sequence data acquisition 3 means may be in wired connection with the computing device 1, or may be able to communicate through a wireless connection, such as e.g. through a network 6, as illustrated. The connection between the computing device 1 and the sequence data acquisition means 3 may be direct or indirect (such as e.g. through a remote computer). The sequence data acquisition means 3 are configured to acquire sequence data from nucleic acid samples, for example genomic DNA samples extracted from cells and/or tissue samples. In some embodiments, the sample may have been subject to one or more preprocessing steps such as DNA purification, fragmentation, library preparation, target sequence capture (such as e.g. exon capture and/or panel sequence capture). Preferably, the sample has not been subject to amplification, or when it has been subject to amplification this was done in the presence of amplification bias controlling means such as e.g. using unique molecular identifiers. Any sample preparation process that is suitable for use in the determination of a genomic copy number profile (whether whole genome or sequence specific) may be used within the context of the present disclosure. The sequence data acquisition means is preferably a next generation sequencer. The sequence data acquisition means 3 may be in direct or indirect connection with one or more databases 2, on which sequence data (raw or partially processed) may be stored.

The following is presented by way of example and is not to be construed as a limitation to the scope of the claims.

EXAMPLES

These examples describe a method of identifying clonal mutations according to the present disclosure, and demonstrate its use using simulated data and multiple types of experimental data.

Methods

Mutational Genotype Model

Figure 4:
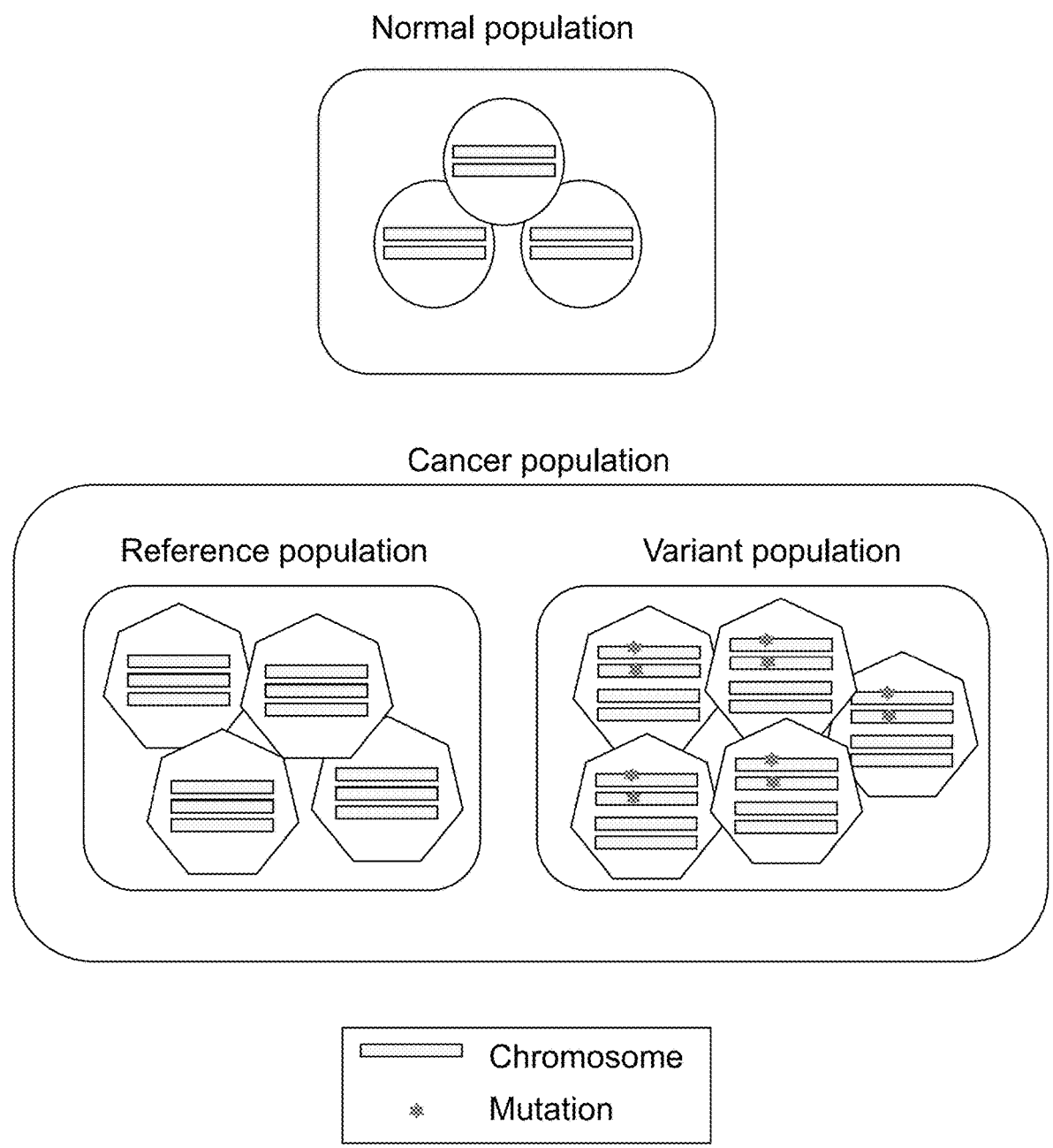
FIG. 4 illustrates schematically the population structured assumed by methods disclosed herein.

The data for the model is allele counts from N mutations (n=1, ... N) from S samples (s=1, ... ,S). For simplicity, and because the method can analyse a single sample and mutation, the indices n for the mutation and s for the sample will not be explicitly included in the notations used this section. As illustrated on FIG. 4, the model assumes that each mutation divides the set of cells that were sequenced into three sub-populations: (i) the normal cell population consisting of cells with healthy germline genomes (likely diploid in the region of the mutation); (ii) the reference cell population which consists of cancer cells without the mutation in question (may be aneuploid in the region of the mutation in question); and (iii) the variant cell population which consists of cancer cells with the mutation in question (may be aneuploid in the region of the mutation in question, may not have the same copy number in said region as the reference population). The term "mutation" is intended here in its broadest sense to refer to any genetic alteration that is detectable in sequence data, and particularly genomic sequence data. This includes in particular single nucleotide variants (SNVs), multiple nucleotide variants (MNVs), indels, etc.

Let G=(A, B, AA, AB, AAA, AABB, ... ) be the set of all genotypes where A and B represent reference and variant alleles respectively. For example, AB would represent a heterozygous variant (comprising one reference/normal allele A and one variant allele B) with total copy number 2. Under this notation, in FIG. 4, the normal population has the genotype AA (where both A can be the same or different, i.e. the normal population may be homozygous or heterozygous, but both alleles are normal), the reference population has the genotype AAA (where the A alleles are selected from the A alleles of the normal population), and the variant population has the genotype AABB (where the A alleles are selected from the A alleles of the normal population and the B alleles are any non-reference alleles). We assume that the genotype of all cells within each sub-population is constant (i.e. by reference to FIG. 4, all cells in the normal population have the genotype AA, all cells in the reference population have the genotype AAA, and all cells in the variant population have the genotype AABB). Let $G=(G_H;G_R;G_V) \in G^3$ be a vector where the entries are the genotype of the normal (healthy), reference and variant populations respectively (each of these individual genotypes will be referred to generically as "G" below). Let t be the proportion of cancer cells in the sample. This is often referred to as the tumour content, tumour purity or cellularity of the sample. Let $\phi$ be the proportion of cancer cells harbouring the mutation in the sample, that is the relative proportion of cancer cells in the variant population. This is often referred to as the cancer cell fraction (CCF) or cellular prevalence of the mutation. Let $\varepsilon$ be the assumed sequencing error rate. The following functions are defined:

a(G): $G \to \mathbb{N}$ is a function which maps a genotype to the number of A alleles (e.g., where G is AA, a(G)=2)

b(G): $G \to \mathbb{N}$ is a function which maps a genotype to the number of B alleles (e.g., where G is AA, b(G)=0)

c(G): $G \to \mathbb{N}$ is a function which maps a genotype to the total copy number at the locus (i.e. c(G)=a(G)+b(G); e.g. where G is AA, c(G)=2)

$\mu$(G): $G \to \mathbb{N}$ is a function which maps a genotype to the value $\mu(G)=\min\{\max\{(b(G)/c(G)), \varepsilon\}, (1-\varepsilon)\}$, which can be interpreted as the probability of sampling a read with the mutation from a population with genotype G.

Let $\xi(G, \phi, t)$ be the probability of sampling a read with the variant allele. Assuming that we have an infinite initial population of cells which are sampled when sequencing, the probability of sampling a read with a variant allele is roughly proportional to the number of copies of the variant allele in the input pool of DNA. More formally, accounting for sequencing error, the probability of sampling a variant allele (given a set of genotypes G, a tumour content t and a cancer cell fraction $\phi$) is given by the following equation (equation (1)):

$$\xi(G, \phi, t) = \tag{1}$$
$$\frac{1}{T}(1-t)c(G_H)\mu(G_H) + \frac{1}{T}t(1-\phi)c(G_R)\mu(G_R) + \frac{1}{T}t\phi c(G_V)\mu(G_V)$$
$$\text{where } T = (1-t)c(G_H) + t(1-\phi)c(G_R) + t\phi c(G_V). \tag{2}$$

The variable $\xi(G, \phi, t)$ captures the sum of the number of copies of the variant allele originating from each genotype multiplied by the probability of sampling a read with a mutation from the genotype, normalised by the sum of the total number of copies of both alleles originating from each genotype.

The variable d is the total number of reads covering the mutation in the sample, of which $d_b$ contain the mutant allele. Thus, the probability of observing these number of reads d, $d_b$ ($P(d, d_b|G, \phi, t)$) can be expressed with a Binomial model with parameters $d_b$ and $\xi(G, \phi, t)$ (equation (3)). This is because the sum of m Bernouilli random variables with parameter p follow a Binomial distribution with parameters m, $p^2$. A Beta-binomial model with mean $\xi(G, \phi, t)$ and precision (inverse of variance) $\gamma$ (equation (4)) can be used instead, for example if the data has more variance than can be explained by a Binomial model:

$$P(d, d_b|G, \phi, t) = \text{Binomial}(d_b|d, \xi(G, \phi, t)) \tag{3}$$

$$P(d, d_b|G, \phi, t, \gamma) = \text{BetaBinomial}(d_b|d, \xi(G, \phi, t), \gamma) \tag{4}.$$

The parameters $\gamma$ is set to 200 in the examples below, though other values are possible. So far, we have assumed that the genotypes of the sub-populations were known. In general this may be true for the healthy population (e.g. from a matched germline sample), but this is not true for the reference and the variant populations. Instead, it is typical to observe allele specific copy number estimates for the region overlapping a mutation. Using this information, we can elicit a prior over a set of plausible genotypes. We explain how to do this in the next section. For now assume we have a vector $\pi$ of prior probabilities where $\pi_i$ is the prior probability of the $i^{th}$ plausible joint genotype, $G_i$, of the populations. We can write the probability of the observed data marginalizing over all plausible genotypes as follows (equations (3a), (4a)):

$$P(d, d_b|\pi, \phi, t) = \Sigma_i \pi_i \text{ Binomial}(d_b|d\xi(G_i, \phi, t)) \tag{3a}$$

$$P(d, d_b|\pi, \phi, t, \gamma) = \Sigma_i \pi_i \text{ BetaBinomial}(d_b|d, \xi(G_i, \phi, t), \gamma) \tag{4a}.$$

In the subsequent sections, the notation $\text{Pr}(d, d_b|\pi, \phi, t)$ will be used to refer equally to the expression of equation (3a) and equation (4a). Note that $\phi$ and t are associated with individual samples so the notation above is a shorthand for $\phi_s$ and $t_s$, respectively.

Eliciting Mutational Genotype Priors

The above model uses either a known joint genotype, or prior probabilities $\pi$, where $\pi_i$ is the prior probability of the $i^{th}$ plausible joint genotype, $G_i$, of the populations (i.e. $G_i$ is one possible combination of genotypes for the healthy, variant and reference populations). Various methods can be used to set potential genotype priors.

For example, one possible method can be referred to as the "major copy number" method. Let $c_{major}$ and $c_{minor}$ denote the major and minor allele copy number for the region overlapping the mutation in the tumour sample. The method "major copy number method" considers two cases:

(a) In the first case, the mutation occurs before the copy number event. In this case the reference population genotype matches the normal population. We consider all possible mutational genotypes for the variant population with up to $c_{major}$ chromosomes containing the variant.

(b) In the second case, the mutation occurs after the copy number event. In this case the reference population has $c_{major}+c_{minor}$ reference alleles. The variant population has 1 variant allele and $c_{major}+c_{minor}-1$ reference allele.

We set the prior weights to be equal for all possible mutational genotypes. For example suppose we have that $c_{major}=2$ and $c_{minor}=1$ and the normal copy number is 2. We have the following possible genotypes:
  $G_1$=(AA, AA, AAB)
  $G_2$=(AA, AA, ABB)
  $G_3$=(AA, AAA, AAB)
each with a prior probability of ⅓. Note that if allele specific copy number is not available then $C_{major}$ can be set to the total copy number and $c_{minor}$ to zero. This approach assumes that a mutation occurs only once, such that if more than one copy of the mutant allele is present in the variant population, then this occurred because the mutation preceded a copy number change at the locus and was subsequently amplified. This approach strikes a good balance between accounting for uncertainty in the genotypes of the populations while not considering too many states.

Alternative approaches may be used for setting the mutational genotype priors. Another possible approach is to simply assume that each mutation is diploid and heterozygous (i.e. the variant in the variant population only occurs on one of the two chromosomes, G=($G_H$=AA, $G_R$=AA, $G_V$=AB)). This may be referred to as "AB prior". Yet another simplistic approach is to assume that each mutation is diploid and homozygous (i.e. the variant in the variant population occurs on both of the two chromosomes, G=($G_H$=AA, $G_R$=AA, $G_V$=BB)). This may be referred to as "BB prior". Yet another possible simple approach is to assume that the genotype of the variant population has the predicted total copy number at the region of the mutation, with exactly one mutant allele (i.e. assuming that the total copy number is 3, G=($G_H$=AA, $G_R$=AA, $G_V$=AAB), i.e. this results in considering only $G_1$ in the "major copy number" method above). This may be referred to as "no zygosity prior". These approaches may be too simplistic in many cases as they essentially consider a single possible genotype.

Another possible approach is to assume that the genotype of the variant population has the predicted total copy number at the region of the mutation, with at least one mutant allele, and that the reference population is either AA or the genotype with a copy number equal to the predicted total copy number and no variant allele (with equal probability). This may be referred to as the "total copy number prior" and intuitively means that the genotype of the variant population at the locus has the predicted total copy number and may have any number (>0) of copies of the mutant allele (i.e. assuming that the total copy number is 3, the possible genotypes are, with equal probabilities, $G_1$=($G_H$=AA, $G_R$=AA, $G_V$=AAB), $G_2$=($G_H$=AA, $G_R$=AA, $G_V$=ABB), $G_3$= ($G_H$=AA, $G_R$=AA, $G_V$=BBB), $G_4$=($G_H$=AA, $G_R$=AAA, $G_V$32 AAB), i.e. this essentially ignores the major and minor copy number values and considers all possible genotypes with n copies—leading to an additional genotype being considered compared to the "major copy number" method above). Yet another approach that can be used is to "trust" the predicted number of major and minor alleles from the copy number caller, such that only genotypes that have a number of mutant alleles corresponding to either the major copy number or the minor copy number are considered. This may be referred to as the "parental" mode. For example, if major copy number=3, minor copy number=1, then this approach would consider the following possible genotypes, with equal probabilities: $G_1$=(AA, AA, AAAB), $G_2$=(AA, AA, ABBB), $G_3$=(AA, AAAA, AAAB) (i.e. either 1 or 3 mutated alleles in the variant population). By contrast, the "major copy number" approach "trusts" the range of the possible major copies, but not the absolute value of it, by considering all values between 1 and the predicted major copy number. With the example above of major copy number=3, minor copy number=1, this would lead to one more genotype being considered compared to the "parental" mode, i.e.: $G_1$=(AA, AA, AAAB), $G_2$=(AA, AA, AABB), $G_3$=(AA, AA, ABBB), $G_4$=(AA, AAAA, AAAB). Thus, the "major copy number" approach strikes a good balance between accounting for additional uncertainty from the copy number calls (compared to the "parental" approach) without having consider too much uncertainty (compared to the "total copy number" approach).

Clonality Estimation Model

This section outlines the hierarchical Bayesian model for identifying ubiquitous mutations. Let Z be a Bernoulli variable which is one when a mutation is ubiquitous (assumed to be clonal) and zero otherwise. Let $\rho$ be the prior probability that the mutation is ubiquitous. This is set to 0.5 in the examples below. As above, $\phi$ is the proportion of cancer cells harbouring the mutation in the sample. Thus, the model can be expressed as:

$$Z|\rho \sim \text{Bernoulli}(Z|\rho) \quad (5)$$

$$\phi|Z \sim \text{Beta}(\phi|\alpha=1, \beta=1) \text{ for } Z=0; \text{Beta}(\phi|\alpha, \beta=1) \text{ for } Z=1 \quad (6)$$

$$d_b, d|\pi, \phi, t \sim Pr(d, d_b|\pi, \phi, t) \quad (7)$$

where $\alpha$ is a parameter>1 in the distribution of $\phi|Z=1$. This is set to $\alpha$=99 in the examples below. A Beta distribution with parameters $\alpha$=99 and $\beta$=1 is skewed towards 1, capturing the assumption that clonal mutations should be enriched for higher cancer cell fraction $\phi$. Other values of the parameter $\alpha$ are possible, though values that capture this assumption are preferred. As mentioned above, the probability in equation (7) is given by equations (3)/(3a) or (4)/(4a).

The joint distribution can be expressed with the following equation (equation (8)):

$$p(d_b, d, \phi, Z=z|\pi, t, \rho) = p(Z=z|\rho)Pr(d_b, d|\pi, \phi, t)p(\phi|Z=z) \quad (8)$$

for one sample, or for a plurality of samples:

$$p(d_b, d, \phi, Z=z|\pi, t, \rho) = p(Z=z|\rho)\Pi_{s=1}^{S} Pr(d_b, d|\pi, \phi, t)p(\phi|Z=z) \quad (8a)$$

The proportion of cancer cells harbouring the mutation ($\phi$) is unknown. However, we can express:

$$p(d_b, d, Z=z|\pi, t, \rho) = \int_0^1 P(d_b, d, \phi, Z=z|\pi, t, \rho)d\phi \quad (9)$$

$$= P(Z=z|\rho)\int_0^1 Pr(d_b, d|\pi, \phi, t)p(\phi|Z=z)d\phi$$

for one sample, or for multiple samples:

$$p(d_b, d, Z=z|\pi, t, \rho) = P(Z=z|\rho)\Pi_{s=1}^{S}\int_0^1 Pr(d_b, d|\pi, \phi, t)p(\phi|Z=z) \quad (9a).$$

The quantity $\Pi_{s=1}^{S}\int_0^1 Pr(d_b, d|\pi, \phi, t)p(\phi|Z)d\phi$ may be referred to as $\psi_z$ (i.e. $\psi_0$ and $\psi_1$ respectively referring to the likelihood of the data if the mutation is non clonal and if the mutation is clonal). As $P(Z=z|\rho)=(1-\rho)$ for z=0 (i.e. the prior probability of Z=0, i.e. the mutation being classified as non-clonal, given a prior probability $\rho$ of the mutation being clonal is equal to the prior probability of the mutation not being clonal), and $P(Z=z|\rho)=\rho$ for z=1 (i.e. the prior probability of Z=1, i.e. the mutation being classified as clonal, given a prior probability of the mutation being clonal of $\rho$ is equal to the prior probability of the mutation being clonal), it follows that:

$$p(d_b, d|\pi, t, \rho) = \sum_{z=0}^{z=1} p(d_b, d, Z=z|\pi, t, \rho) \quad (10)$$

$$= (1-\rho)\prod_{s=1}^{S}\int_0^1 Pr(d_b, d|\pi, \phi, t)p(\phi|Z=0)d\phi +$$

$$\rho\prod_{s=1}^{S}\int_0^1 Pr(d_b, d|\pi, \phi, t)p(\phi|Z=1)d\phi$$

for multiple samples (without the product over samples for a single sample).

Ultimately, the quantity that we wish to estimate is the probability of a mutation being clonal (probability that Z=1), in view of the reads observed ($d_b$, d), a genotype prior ($\pi$), a tumour fraction estimate (t), and a prior probability of the mutation being clonal ($\rho$, i.e. we want to estimate $P(Z=1|d_b, d, \pi, t, \rho)$). In view of the above, this can be expressed as:

$$p(Z=z|d_b, d, \pi, t, \rho) = \frac{p(d_b, d, Z=z|\pi, t, \rho)}{p(d_b, d|\pi, t, \rho)} \quad (11)$$

where $p(d_b, d|\pi, t, \rho)$ is given by equation (10) and $p(d_b, d, Z=z|\pi, t, \rho)$ is given by equations (9)/(9a). Thus, equation (11) can be written for Z=1 as equation (11a) below:

$$p(Z=1|d_b, d, \pi, t, \rho) = \quad (11a)$$

$$\frac{\rho\prod_{s=1}^{S}\int_0^1 Pr(d_b, d|\pi, \phi, t)p(\phi|Z=1)d\phi}{(1-\rho)\prod_{s=1}^{S}\int_0^1 Pr(d_b, d|\pi, \phi, t)p(\phi|Z=0)d\phi + \rho\prod_{s=1}^{S}\int_0^1 Pr(d_b, d|\pi, \phi, t)p(\phi|Z=1)d\phi}$$

where ρ is a parameter (set to 0.5 in the examples below), $p(\phi|Z=z)$ is given by the beta distributions in equation (6), and $Pr(d_b, d|\pi, \phi, t)$ is given by equations (3)/(4) (one joint genotype) or (3a)/(4a) (plurality of candidate joint genotypes with prior probabilities π).

Thus, estimating equation (11) for z=1 (i.e. equation (11a)) gives us the probability that a mutation is ubiquitous (i.e. assumed to be clonal in view of the one or more samples available). This requires evaluating S one dimensional integrals (one for each sample, in equations (9), (10)), which can be done efficiently using known numerical integration. Any numerical integration algorithm known in the art may be used for this purpose. For example, a grid approximation may be used. This is advantageously simple, and sufficient considering that there is a single parameter (φ) to integrate over.

This provides an estimate of the probability that a mutation is clonal in view of the data available, which can be efficiently computed, is readily interpretable (in view of the rigorous statistical model making use of explicit clear assumptions), can be obtained for any mutation without manual input, is independent of any other mutation analysed, can rigorously include prior knowledge about the mutation, and can be used to objectively and automatically prioritise a list of mutations (with accompanying probabilities) for testing and/or use.

Accounting for Uncertainty in Copy Number Predictions

While the model described above already presents numerous advantages, it can be further enhanced by taking into account uncertainties in the prediction of the copy number estimates used in the model. Indeed, the above model assumes that the copy numbers (e.g. the major/minor/total/copy numbers used to elicit the genotype priors) were accurately predicted. In practice there may be some uncertainty in these values. Indeed, the problem of allele-specific copy number analysis of tumours is complex and many solutions have been proposed to do this. One commonly used approach is ASCAT (allele-specific copy number analysis of tumors, Van Loo et al., 2010), which takes into account both aneuploidy of the tumour cells and non-aberrant cell infiltration in interpreting a bulk copy number profile, and outputs estimated allele-specific copy number profiles and accompanying tumour purity estimates. In short, ASCAT evaluates a plurality of possible combinations of tumour ploidy and tumour fractions, based on the assumption that the associated allele-specific copy number calls should be as close as possible to nonnegative whole numbers for germline heterozygous single nucleotide polymorphisms (SNPs). A solution deemed optimal is then reported (estimated tumour ploidy, tumour purity and allele-specific copy number calls for the tumour and normal part of the sample) together with its goodness-of-fit (based on the above assumption).

The model provided above can be adjusted to accommodate multiple copy number solutions and their uncertainties, by modifying π to contain entries for the genotypes from each predicted copy number state (e.g. each proposed solution comprising a major and minor copy state), weighted by the probability associated with this state. Additionally, as the tumour purity estimate may be estimated together with these copy number states (as is the case e.g. when an approach like ASCAT is used), the associated tumour purity estimate can also be taken into account. Note that this may not be necessary when e.g. the tumour purity is estimated or measured separately and is not intrinsically associated with the copy number state estimate. Nevertheless, for the sake of generality, let us assume that we have a set of C possible copy number/tumour content states (e.g. C possible sets of estimates of $c_{major}$, $c_{minor}$, and t). Let $\pi_C$ be a vector where each entry is the probability for each possible such set of estimates. For each state C, it is possible to compute the vector $\pi_{CG}$ of possible genotypes as explained above. A final genotype vector can thus be obtained by multiplying $\pi_{CG}$ by the entry for state C in $\pi_C$. This gives rise to the slightly modified equations below:

$$P(d, d_b|\pi, \phi) = \Sigma_i \pi_i \text{ Binomial}(d_b|d, \xi(G_i, \phi, t_i)) \quad (3b)$$

$$P(d, d_b|\pi, \phi, \gamma) = \Sigma_i \pi_i \text{ BetaBinomial}(d_b|d, \xi(G_i, \phi, t_i), \gamma) \quad (4b)$$

where the tumour content $t_i$ may now depend on the particular state (and the $\pi_i$ are elements of the vector π obtained by multiplying $\pi_{CG}$ by the entry for state C in $\pi_C$). These new densities can be substituted in the relevant equations above. In particular, the problem solved may then be expressed as solving equation (11a), where $Pr(d_b, d|\pi, \phi, t)$ is given by equation (3b) or equation (4b). The values for $t_i$, $c_{major}$, $c_{minor}$ (and hence the compatible $\pi_{CG}$ according to the model used) and $\pi_C$ are provided as outputs of many methods for performing allele-specific copy number analysis of tumours, including but not limited to ASCAT, as explained above. For the avoidance of any doubt, any approach that generates allele-specific copy number state estimates (typically with associated with a tumour purity estimate) with a confidence or other metric that can be used to weight multiple solutions relative to each other may be used for this purpose.

Implementation

The methods described herein may be implemented using any programming language known in the art. In the examples below, a Python script implementing the above method was used. This took as input, for each mutation: a mutation identifier, a sample identifier, a count of the number of reads that match the reference allele at the mutation position, a count of the number of reads that match the alternate allele at the mutation position, and, for each of one or more copy number solutions: the major copy number (for the tumour) overlapping the mutation for the specified copy number solution, the minor copy number (for the tumour) overlapping the mutation for the specified copy number solution, a copy number for the normal cell at the mutation (may be set to default=2 for autosomal chromosomes, or 1 for a sex chromosome in a male subject), and a tumour purity value for the specified copy number solution (this can also be obtained as an output of e.g. ASCAT, or can be separately obtained). The major and minor copy number overlapping the mutation for the tumour population, for a specified copy number solution, can be obtained directly from ASCAT (e.g. using ascatNgs, Raine et al., 2016), or derived from the output of e.g. ASCAT such as using the mean B allele frequency of the copy number segment overlapping the mutation, the log R value of the copy number segment overlapping the mutation, and the ploidy of the solution. For example, the allele specific copy number estimates ($\hat{n}_A$, $\hat{n}_B$) for the tumour at a location i can be expressed as functions of the log R value rat location i, the B allele fraction value b at location i, the ploidy estimate ψ, the tumour cell fraction estimate ρ, and a platform-dependent "technology" parameter t (which can be set to t=1 for next generation sequencing data such as WES) using:

$$\hat{n_A} = \left(\rho - 1 + 2^{\frac{r}{\gamma}}(1-b)(2(1-\rho) + \rho\psi)\right)/\rho \text{ and}$$

$$\hat{n_B} = \left(\rho - 1 + 2^{\frac{r}{\gamma}}b(2(1-\rho) + \rho\psi)\right)/\rho.$$

The major and minor copy numbers in the normal population may be assumed to be 1 and 1, apart from mutations on the sex chromosomes which may be handled depending on the sex of the subject. Where multiple copy number solutions are provided, a probability of each solution may optionally be provided (this can also be obtained from the output of e.g. ASCAT which proves a negative log likelihood for a solution). If this is not provided, then all of a plurality of solutions may be treated as equally likely and receive equal weight. The script produced as output a mutation identifier and posterior probability that the mutation is ubiquitous.

In the examples below, whenever a copy number solution was estimated this was done using ASCAT (Van Loo et al., 2010).

Results

Synthetic Data

The approach described above was first tested using synthetic data simulated using the population model described above by reference to FIG. 4 as captured by equations (3) (Binomial model) and (4) (Beta-Binomial model). A total of 1000 mutations were simulated for all synthetic data sets. The depth of coverage was simulated from Poisson distributions with mean values 50, 100, 1000 corresponding to realistic coverage regimes. Copy number profiles were simulated randomly with a maximum total copy of two or six. These settings correspond to a genomically stable genome (maximum total copy number of two) and a highly aneuploid genome (maximum total copy number of 6). Data sets comprising one, two or four samples were simulated. Tumour content was fixed at 1.0 for all examples.

Figure 5A:
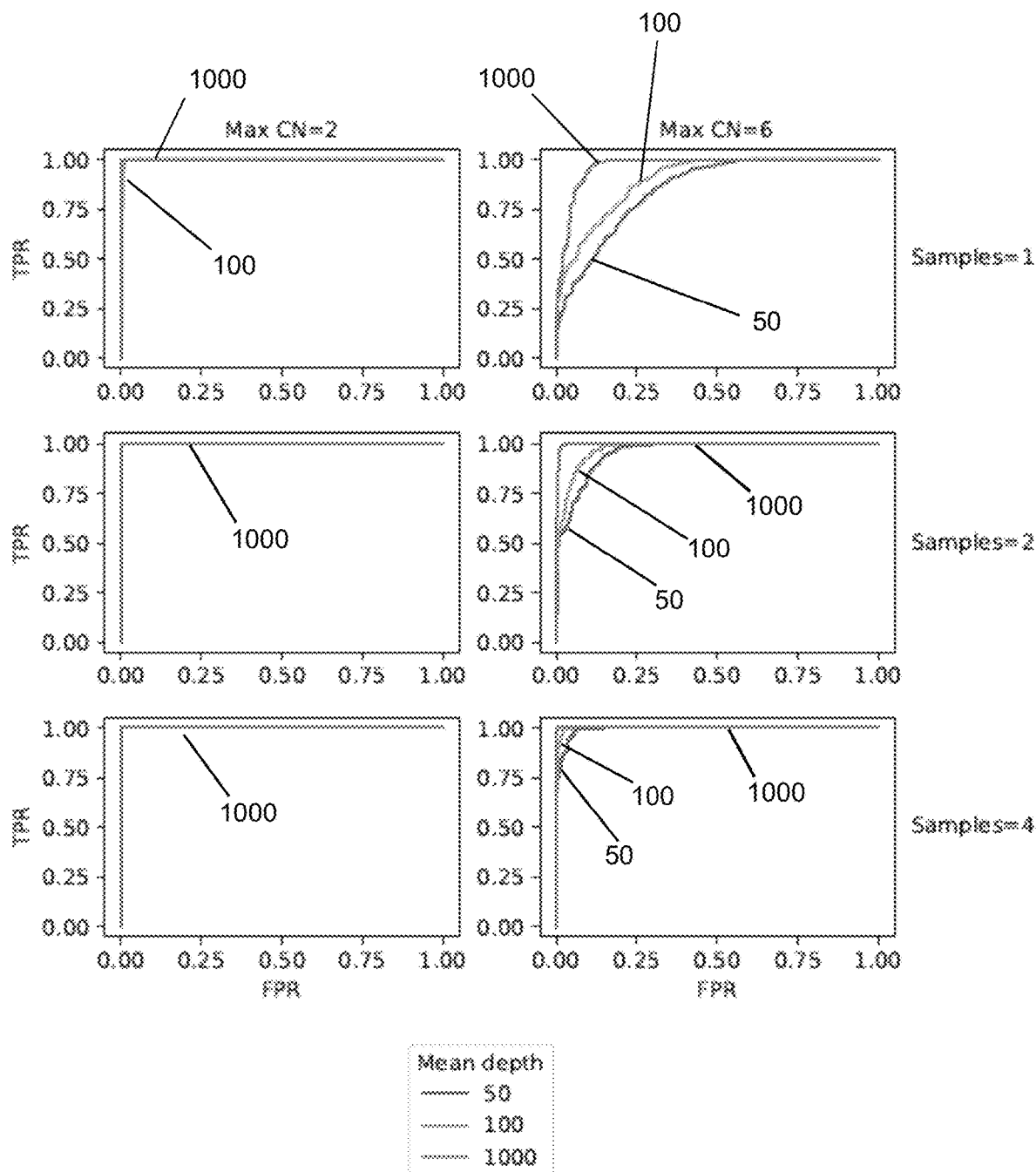
FIGS. 5A, 5B and 5C show the results of a method of identifying clonal mutations described herein, using synthetic data. Each plot shows ROC curves (receiver operating characteristic, True positive rate (TPR=TP/(TP+FN) where TP=number of true positives, FN=number of true negatives; sensitivity) as a function of False positive rate (FPR=FP/(FP+TN), where FP=number of false positives, TN=number of true negatives; 1-specificity) for a different maximum copy number and number of samples, with 3 separate curves each showing a different simulated read depth. A. Binomial emission model used for simulation and identification. B. Beta-binomial emission model used for simulation, Binomial model used for identification. C. Beta-binomial emission model used for simulation and identification.

FIG. 5A shows the results when the data is simulated from a Binomial model and the above method is run using a Binomial model. For the copy number two runs, performance is nearly perfect regardless of depth or the number of samples (area under the curve, AUC=0.997-1.0, see Table 1 below). For the copy number six runs performance is considerably improved as depth and the number of samples increases (AUC=0.853-1.0, see Table 1 below).

TABLE 1

Synthetic data results using a Binomial distribution model for simulation. BB-200 = BetaBinomial, γ = 200.

| Model used in analysis | Max copy number | mean depth | S (number of samples) | AUC |
|---|---|---|---|---|
| BB-200 | 2 | 50 | 1 | 0.9975431554 |
| Binomial | 2 | 50 | 1 | 0.9975431554 |
| BB-200 | 2 | 100 | 1 | 0.9981312525 |
| Binomial | 2 | 100 | 1 | 0.9981312525 |
| BB-200 | 2 | 1000 | 1 | 1 |
| Binomial | 2 | 1000 | 1 | 1 |
| BB-200 | 2 | 50 | 2 | 1 |
| Binomial | 2 | 50 | 2 | 1 |
| BB-200 | 2 | 100 | 2 | 1 |
| Binomial | 2 | 100 | 2 | 1 |
| BB-200 | 2 | 1000 | 2 | 1 |

TABLE 1-continued

Synthetic data results using a Binomial distribution model for simulation. BB-200 = BetaBinomial, γ = 200.

| Model used in analysis | Max copy number | mean depth | S (number of samples) | AUC |
|---|---|---|---|---|
| Binomial | 2 | 1000 | 2 | 1 |
| BB-200 | 2 | 50 | 4 | 1 |
| Binomial | 2 | 50 | 4 | 1 |
| BB-200 | 2 | 100 | 4 | 1 |
| Binomial | 2 | 100 | 4 | 1 |
| BB-200 | 2 | 1000 | 4 | 1 |
| Binomial | 2 | 1000 | 4 | 1 |
| BB-200 | 6 | 50 | 1 | 0.852432188 |
| Binomial | 6 | 50 | 1 | 0.852540223 |
| BB-200 | 6 | 100 | 1 | 0.9012136777 |
| Binomial | 6 | 100 | 1 | 0.90078165 |
| BB-200 | 6 | 1000 | 1 | 0.961997085 |
| Binomial | 6 | 1000 | 1 | 0.9687399898 |
| BB-200 | 6 | 50 | 2 | 0.9570949962 |
| Binomial | 6 | 50 | 2 | 0.9567547662 |
| BB-200 | 6 | 100 | 2 | 0.9732051405 |
| Binomial | 6 | 100 | 2 | 0.9741773894 |
| BB-200 | 6 | 1000 | 2 | 0.9962227762 |
| Binomial | 6 | 1000 | 2 | 0.9977032559 |
| BB-200 | 6 | 50 | 4 | 0.9923878205 |
| Binomial | 6 | 50 | 4 | 0.9924078526 |
| BB-200 | 6 | 100 | 4 | 0.9974953588 |
| Binomial | 6 | 100 | 4 | 0.9978354459 |
| BB-200 | 6 | 1000 | 4 | 0.9995103528 |
| Binomial | 6 | 1000 | 4 | 0.999959865 |

Figure 5B:
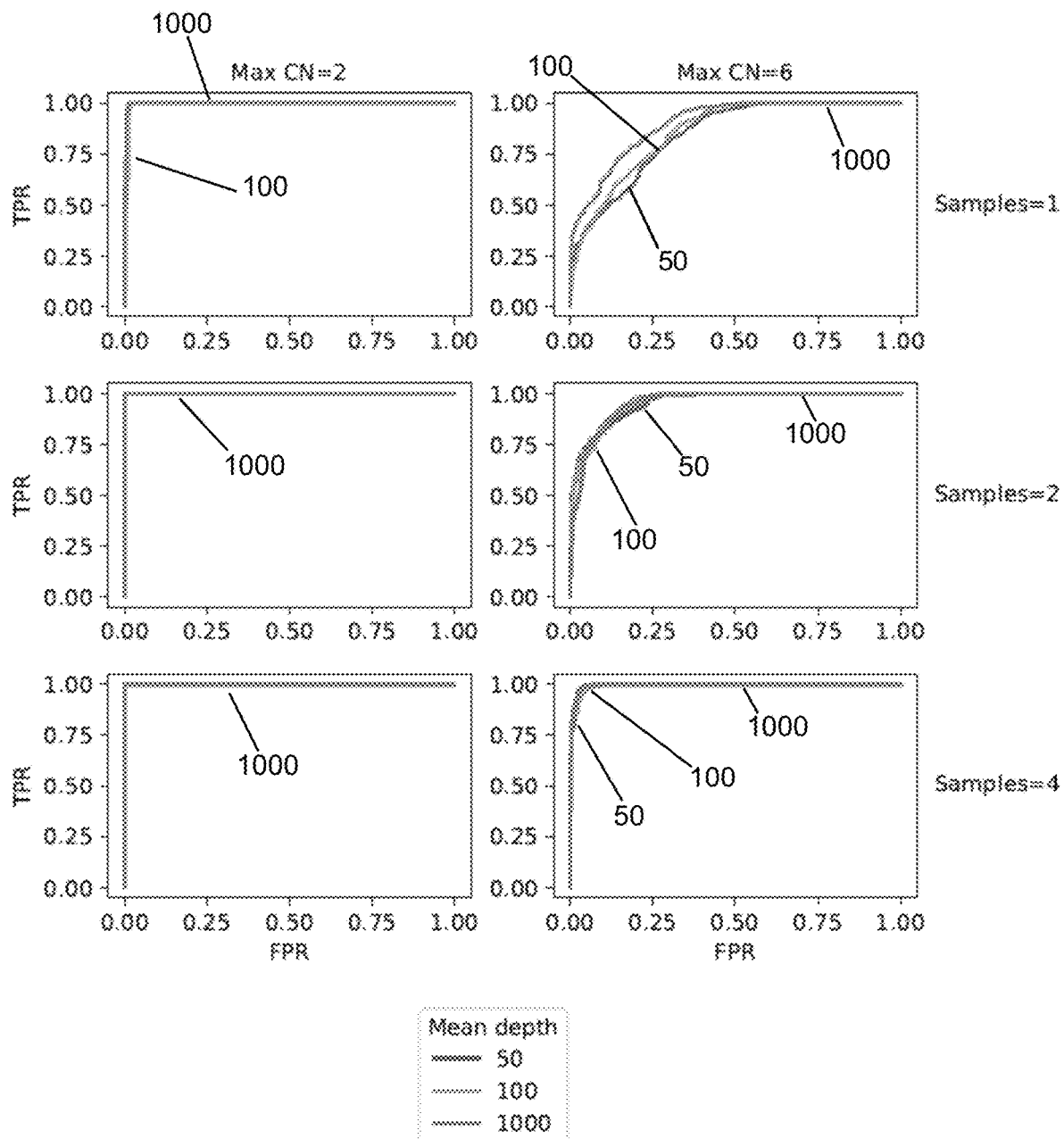

FIG. 5B shows the same analysis done by simulating from a Beta-Binomial distribution with precision 100 and with the above model run using a Binomial emission model. This simulates the case where the observed data is significantly more variable than expected. The results remain nearly perfect for the copy number two simulations (AUC 0.997-1.0, Table 2). However, the results (while remaining good) are not as good as the previous analysis for the copy number six simulations (AUC 0.846-0.996, Table 2). Increasing the depth of coverage does not improve performance as significantly as before. In contrast increasing the number of samples has a substantial effect.

Figure 5C:
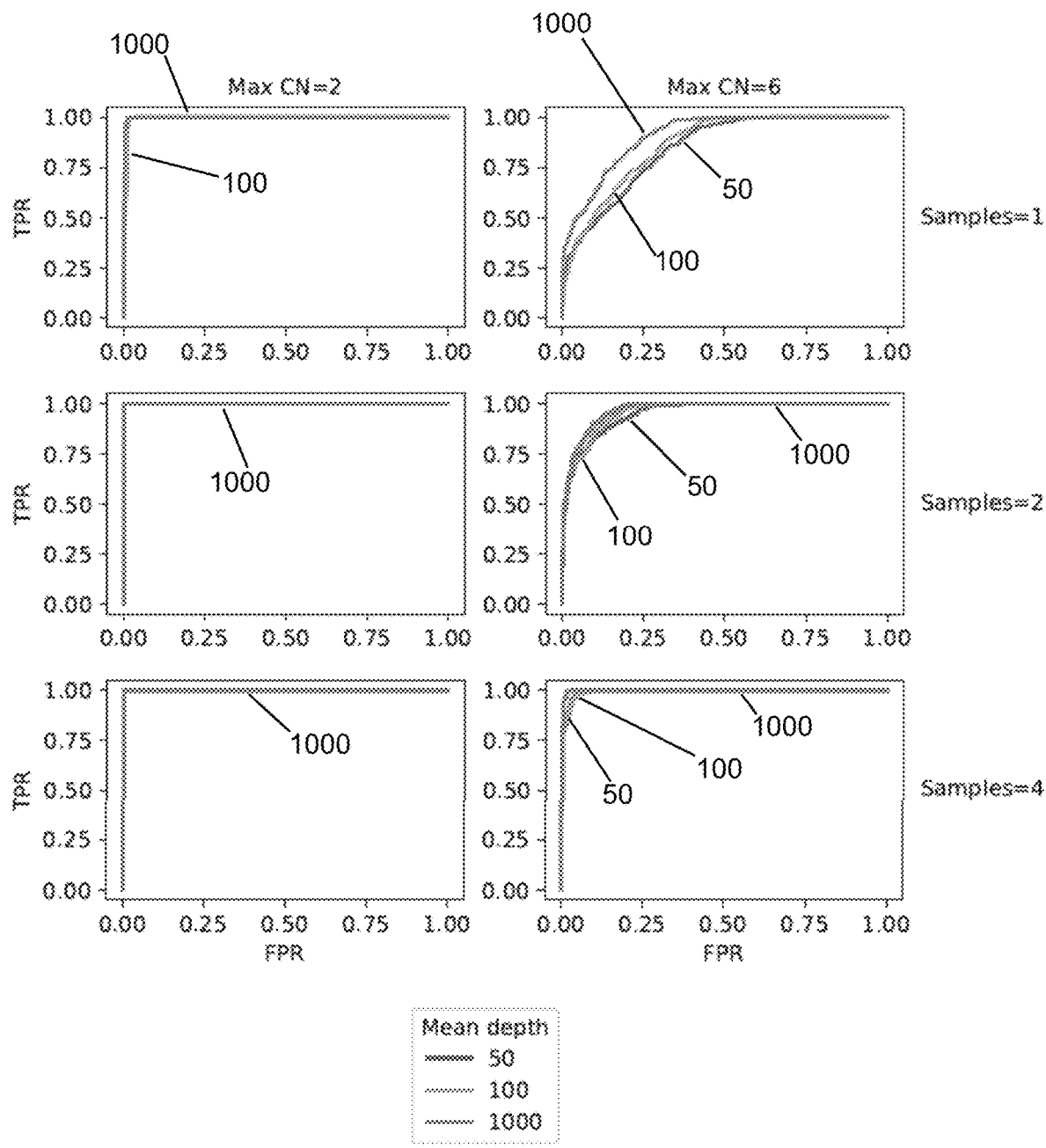

FIG. 5C shows the results when the data is simulated using a Beta-Binomial distribution with precision 100 and analysed with the above method using a Beta-Binomial emission model with precision 200. Performance is similar to the previous analysis using the above method with a Binomial emission (Table 2). Using the Beta-Binomial model on over-dispersed data did perform slightly better especially at lower sequencing depths and/or higher copy numbers, compared to using the Binomial model on the same over-dispersed data. However, in this example the improvement in performance was not significant and the simpler Binomial model (which is simpler to parameterise since a precision hyperparameter does not need to be set) could therefore be advantageously used in both cases.

TABLE 2

Synthetic data results using a Beta-Binomial emission distribution with precision 100 for simulation. BB = BetaBinomial

| Model used in analysis | Max copy number | mean depth | S (number of samples) | AUC |
|---|---|---|---|---|
| BB-200 | 2 | 50 | 1 | 0.9975810324 |
| Binomial | 2 | 50 | 1 | 0.9975810324 |
| BB-200 | 2 | 100 | 1 | 0.9935050647 |
| Binomial | 2 | 100 | 1 | 0.9935050647 |
| BB-200 | 2 | 1000 | 1 | 0.9983754737 |

TABLE 2-continued

Synthetic data results using a Beta-Binomial emission distribution with precision 100 for simulation. BB = BetaBinomial

| Model used in analysis | Max copy number | mean depth | S (number of of samples) | AUC |
|---|---|---|---|---|
| Binomial | 2 | 1000 | 1 | 0.9983754737 |
| BB-200 | 2 | 50 | 2 | 1 |
| Binomial | 2 | 50 | 2 | 1 |
| BB-200 | 2 | 100 | 2 | 0.9999919783 |
| Binomial | 2 | 100 | 2 | 0.9999919783 |
| BB-200 | 2 | 1000 | 2 | 1 |
| Binomial | 2 | 1000 | 2 | 1 |
| BB-200 | 2 | 50 | 4 | 1 |
| Binomial | 2 | 50 | 4 | 1 |
| BB-200 | 2 | 100 | 4 | 1 |
| Binomial | 2 | 100 | 4 | 1 |
| BB-200 | 2 | 1000 | 4 | 1 |
| Binomial | 2 | 1000 | 4 | 1 |
| BB-200 | 6 | 50 | 1 | 0.8460939595 |
| Binomial | 6 | 50 | 1 | 0.8455535942 |
| BB-200 | 6 | 100 | 1 | 0.8628064402 |
| Binomial | 6 | 100 | 1 | 0.859359738 |
| BB-200 | 6 | 1000 | 1 | 0.908828000 |
| Binomial | 6 | 1000 | 1 | 0.899468000 |
| BB-200 | 6 | 50 | 2 | 0.955679568 |
| Binomial | 6 | 50 | 2 | 0.9547434743 |
| BB-200 | 6 | 100 | 2 | 0.9603051358 |
| Binomial | 6 | 100 | 2 | 0.9590724257 |
| BB-200 | 6 | 1000 | 2 | 0.9685954382 |
| Binomial | 6 | 1000 | 2 | 0.9525490196 |
| BB-200 | 6 | 50 | 4 | 0.9944876472 |
| Binomial | 6 | 50 | 4 | 0.9943236367 |
| BB-200 | 6 | 100 | 4 | 0.9937650015 |
| Binomial | 6 | 100 | 4 | 0.9932320614 |
| BB-200 | 6 | 1000 | 4 | 0.9990039641 |
| Binomial | 6 | 1000 | 4 | 0.9961278606 |

Cell Line Mixture Data

The method was next tested using data generated by mixing cell lines (Farahani et al., 2017). Data was obtained from two experiments where: 1) diploid cell lines were mixed and 2) aneuploid cell lines were mixed. Multiple mixtures were formed in varying proportions as described in Table 3. Three classes of mutations are present in each experiment: 1) mutations unique to cell line A; 2) mutations unique to cell line B and 3) mutations shared by both cell lines. For the purposes of testing the methods described herein the mutations which were shared were treated as the ubiquitous mutations and the cell line specific mutations were treated as the subclonal mutations. Allele count data and copy number information was extracted from supplementary tables S1A and S1B of Farahani et al. which were downloaded from the publisher's website. Note that it was not possible to account for uncertainty in copy number with this data, as only predicted major/minor copy is given for each mutation.

The method described above run with the Binomial emission model was compared to PyClone (Roth et al., 2014) version 0.13.1 run for 10,000 iterations with 1,000 iterations discarded as burning. To identify ubiquitous mutations with PyClone, the cluster with the highest CCF across all samples was first identified. All mutations in this cluster were treated as ubiquitous and all other mutations were treated as subclonal. Note that this strategy does not assign a confidence value to predictions of ubiquity, thus PyClone results are plotted as a single point on the ROC curves. In contrast, the methods described herein assign a probability of ubiquity to each mutation so it is possible to plot a curve. Thus, it is also possible to tune a threshold used to consider mutations as clonal/subclonal depending on a desired balance of precision and recall.

TABLE 3

| Cell line mixture proportions | | |
|---|---|---|
| Mixture ID | Cell line A | Cell line B |
| 2 | 0 | 1 |
| 14 | 0 | 1 |
| 7 | 0.1 | 0.9 |
| 19 | 0.1 | 0.9 |
| 6 | 0.25 | 0.75 |
| 18 | 0.25 | 0.75 |
| 5 | 0.5 | 0.5 |
| 17 | 0.5 | 0.5 |
| 4 | 0.75 | 0.25 |
| 16 | 0.75 | 0.25 |
| 3 | 0.9 | 0.1 |
| 15 | 0.9 | 0.1 |
| 1 | 1 | 0 |
| 13 | 1 | 0 |

Figure 6A:
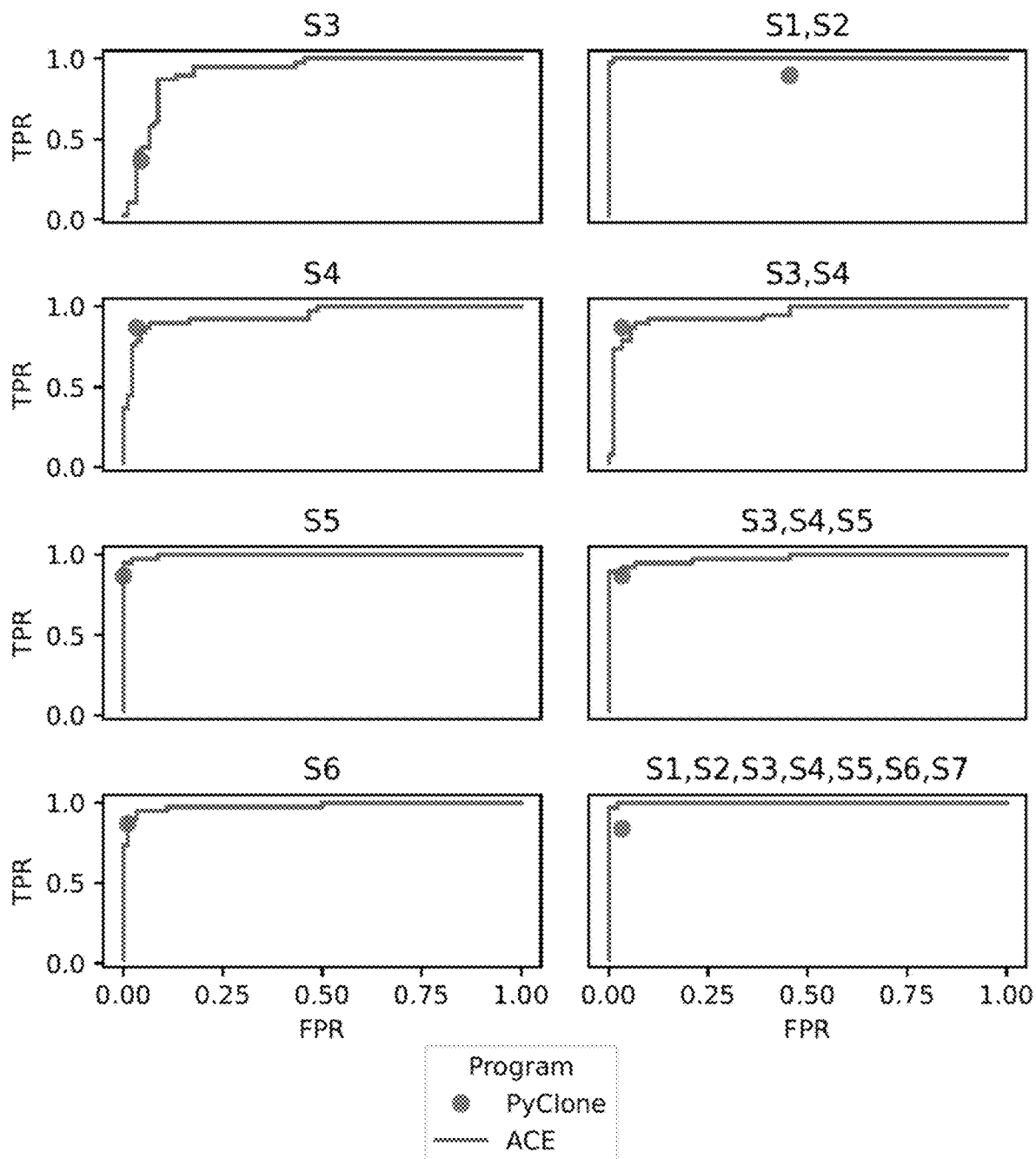
FIGS. 6A and 6B show the results of a method of identifying clonal mutations described herein, using data from cell line mixing experiments with a diploid cell line (A) and an aneuploid cell line (B). The title of each plot indicates which samples where included in the analysis. Each plot shows the ROC curve using a method as described herein (labelled "ACE"), and a single point showing the TPR and FPR obtained when running PyClone (Roth et al., 2014) on the same data.
Figure 6B:
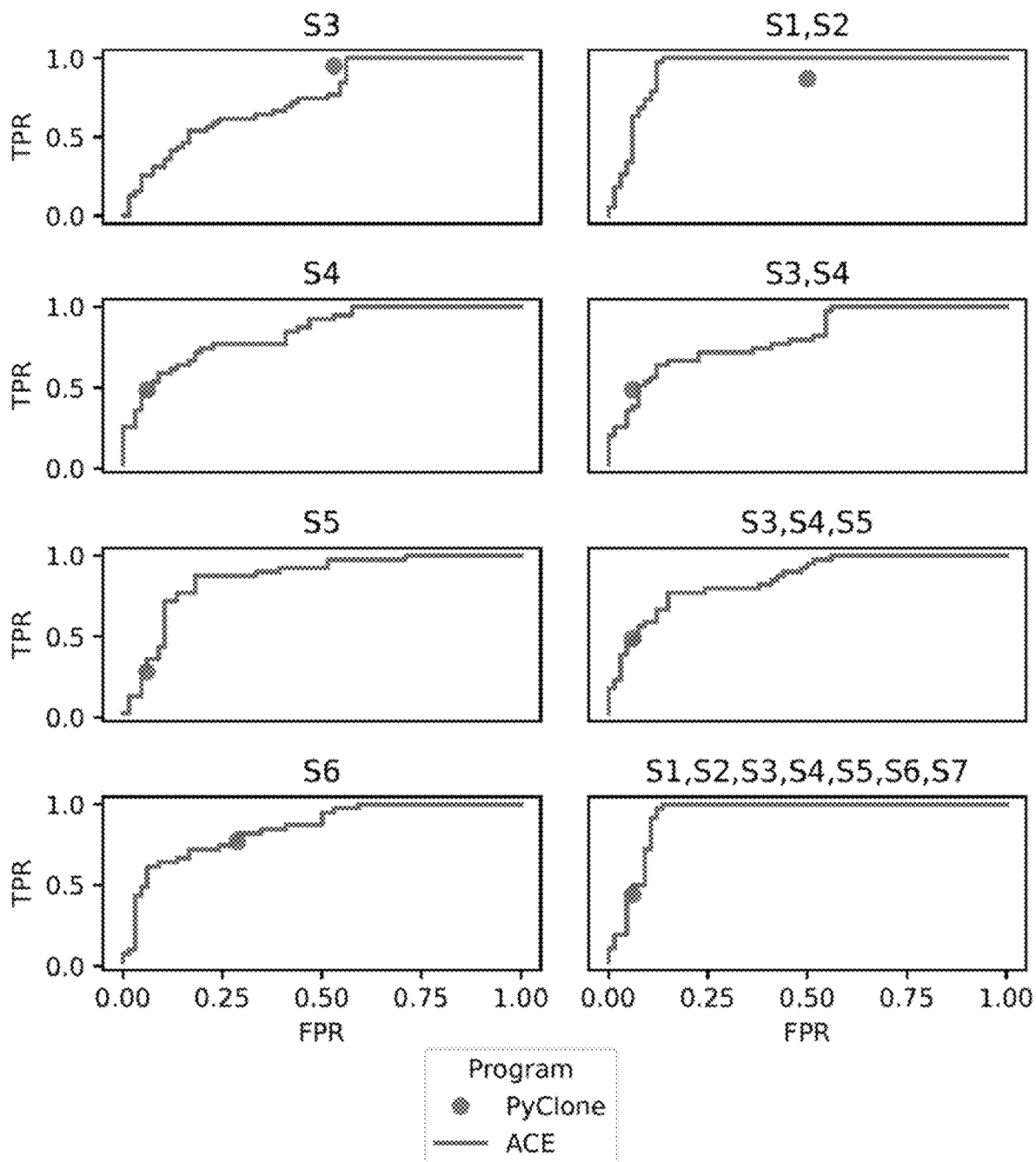

FIG. 6A shows the results for the diploid cell line mixtures. The plots on the left of FIG. 6A are from runs using only single samples. They are worst for both approaches using mixture S3 which is 90% cell line A and 10% cell line B. This makes sense as the mutations from cell line A would have a CCF close to the shared mutations. Performance increases as the mixtures become more balanced and the CCF of mutations in the cell lines move away from 1. The right of FIG. 6A shows the results from runs using multiple samples. FIG. 6B shows the results from the mixture of aneuploid cell lines. The results are generally concordant with the diploid case, though performance is uniformly worse for both approaches as expected.

This data indicates that, as expected, performance is likely to increase as more samples are added. In the particular set up of the simulated data and artificial samples analysed here, performance of the methods described herein and the PyClone were similar for some samples, but the methods described herein outperformed PyClone in some multi-sample instances.

An informal timing study for each method revealed the methods described herein took approximately 10 seconds per analysis (where an analysis comprises determining the likelihood of clonality for all of the mutations identified in a patient). PyClone took significantly longer for the same analysis, on the order 300-3000 seconds depending on the number of MCMC iterations performed. Thus, even when all of the mutations identified in a patient are assessed in the same analysis (which is not a requirement of the present method as these assessments are completely independent), the present method is at least 30 times faster than the prior art method. The difference could be even larger if assessment of the mutations was performed in parallel instead of in series, which is not possible using the prior art method.

Thus, this data demonstrates that the approach described herein is able to at least match, and outperform a comparative state-of-the-art approach in multi-samples cases. These are of great clinical and practical relevance as acquiring multiple samples where possible is believed to be likely to increase the likelihood of identifying truly clonal variants when using a method that can take advantage of it, such as the methods described herein. In contrast to the methods described herein, PyClone does not have the ability to provide a mutation-specific prediction, to provide a confidence estimate for each such prediction, or to take into account uncertainty in copy number solutions, and requires manual input as well as significantly more computational time to analyse the same data.

Thus, the methods described herein have several advantages compared to the methods of the prior art, which are particularly relevant in a practical clinical context, in addition to the specific cases where the methods of the prior art could be used with similar performance (such as the simulated and artificial samples above). For example, the requirement for extensive manual input at least in curating and selecting a single copy number solution means that without such expert input the methods described herein would perform significantly better than the method of the prior art even in single sample situations. Further, even with expert manual input available, the methods described herein would perform significantly better than the method of the prior art in real life situations (i.e. using actual tumour samples from patients) where identifying the correct copy number solution is significantly more error-prone than in the artificial, controlled situations investigated above.

TRACERx Data

Figure 7A:
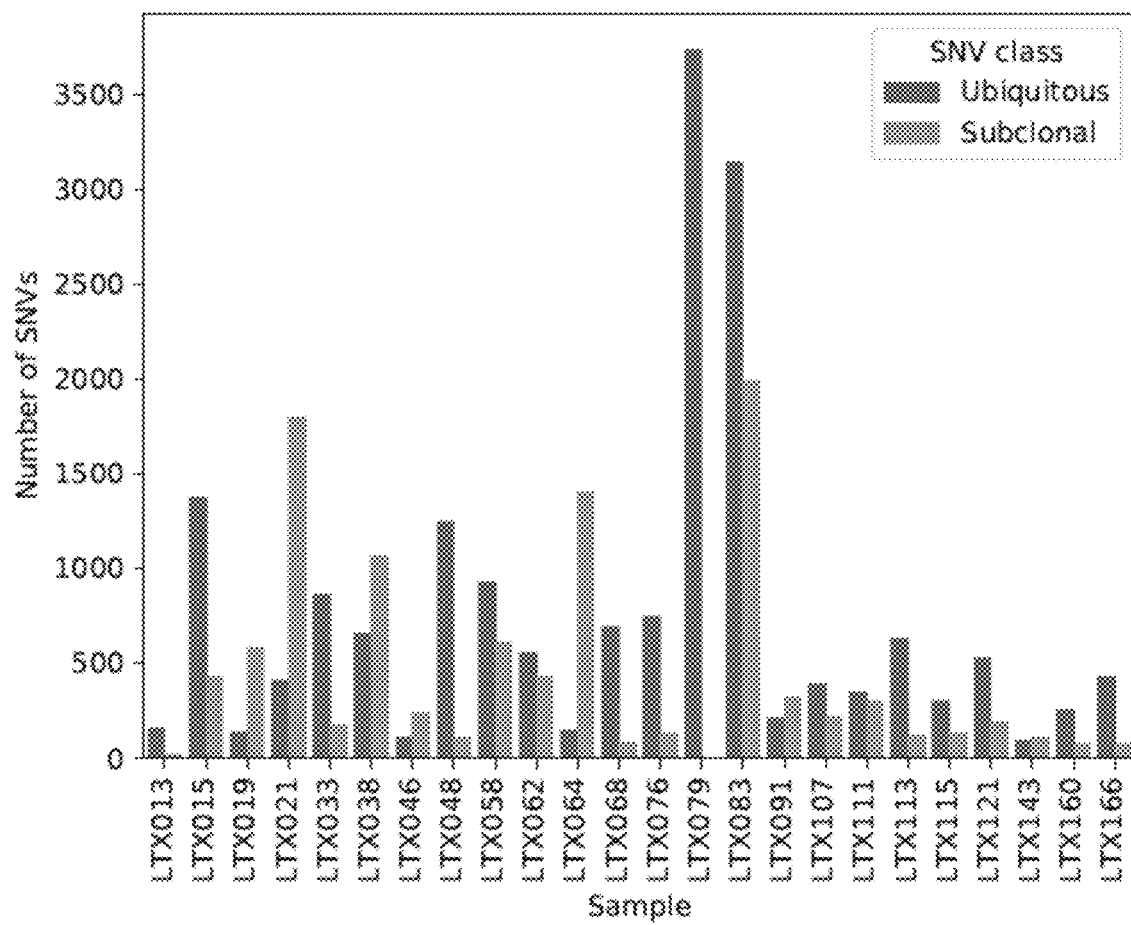
FIGS. 7A, 7B and 7C show the results of a method of identifying clonal mutations described herein, using data from the TRACERx project. A. Overview of the data analysed. For each sample, the numbers of clonal and subclonal SNVs identified using the TRACERx pipeline (manually curated PyClone results) are shown. B. Distribution of predicted ubiquitous probabilities from a method as described herein. (Left) Results when all ASCAT (Van Loo et al., 2010) ploidy/purity solutions are considered weighted by probability. (Right) Results when the most likely solution from ASCAT is selected. C. ROC curves illustrating the predictive performance of a method as described herein (with or without taking into account all possible solutions from ASCAT weighted by probability) using manually curated PyClone (Roth et al., 2014) calls as ground truth.

The methods described herein were further tested on data from the CRUK TRACERx study (tracerx.co.uk). This data had previously been analysed using the TRACERx pipeline (see McGranahan et al., 2016), and clonal calls based on the PyClone method were available. In addition, ASCAT data for ploidy/purity solutions were available for all samples. An overview of the data is shown on FIG. 7A (based on the clonal calls available, obtained using PyClone). Thus it was possible to run the present method accounting for uncertainty over the selected ploidy/purity solution used to derive major/minor copy numbers.

Figure 7B:
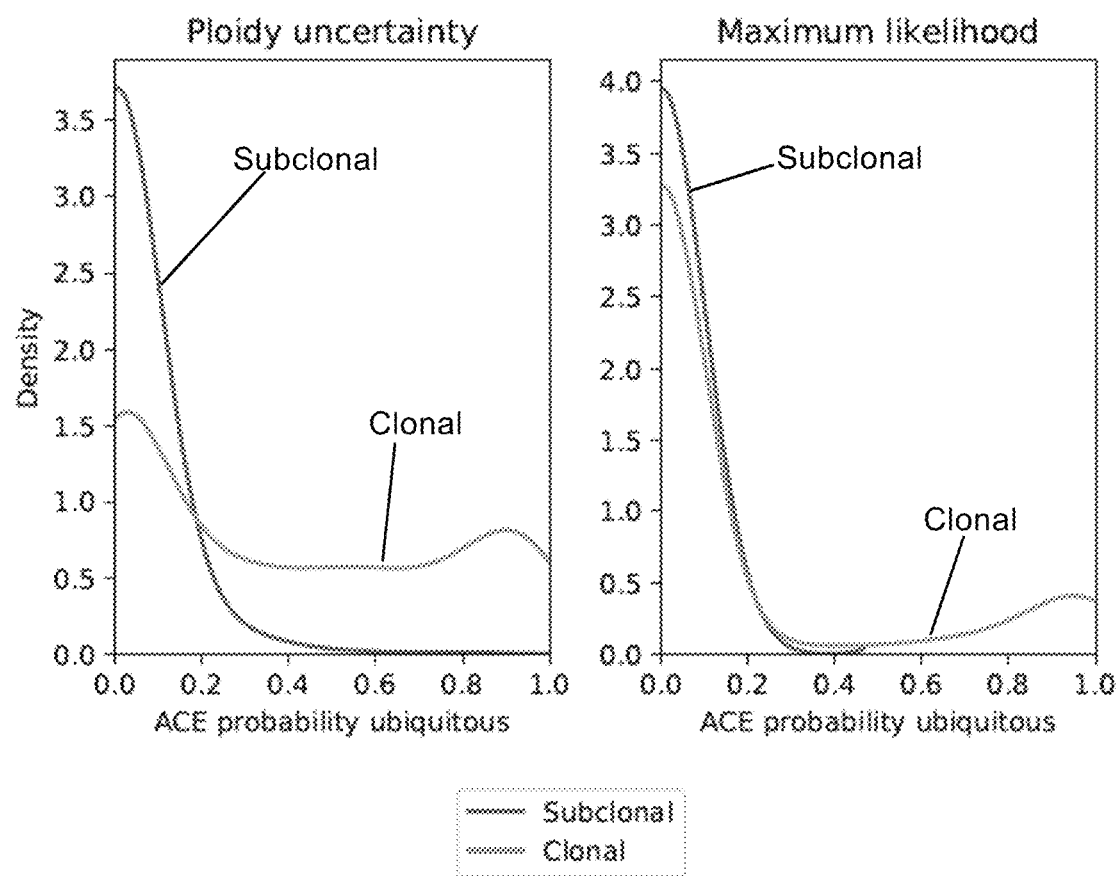
Figure 7C:
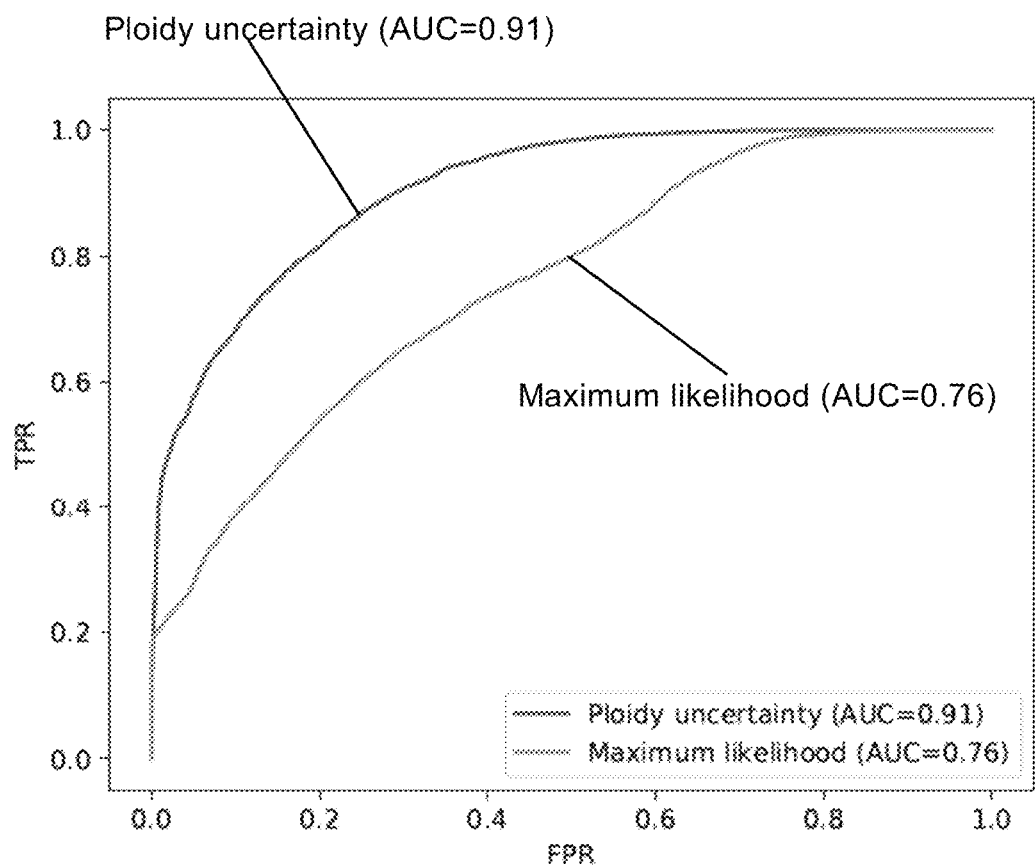

FIG. 7B shows the distribution of predicted ubiquitous probabilities from the methods described herein when 1) all ASCAT purity/ploidy solutions are considered and 2) when the maximum likelihood ASCAT solution is considered. We see that the present method systematically assigned higher probability to ubiquitous mutations when purity/ploidy uncertainty was considered. FIG. 7C shows the ROC curve comparing the two approaches. Accounting for uncertainty in ploidy and purity significantly improved the performance of the present method with the AUC going from 0.76 to 0.91. One caveat of this analysis is that the curated PyClone results were assumed as truth (as no ground truth can be obtained, contrary to the simulated data and artificial samples analysed above). The previous section suggests that the methods described herein outperform PyClone for real tumour samples and multi-samples situations, so actual performance of the methods described herein is likely to be better than reported here.

Runtime Comparisons with Prior Art Method

Figure 8:
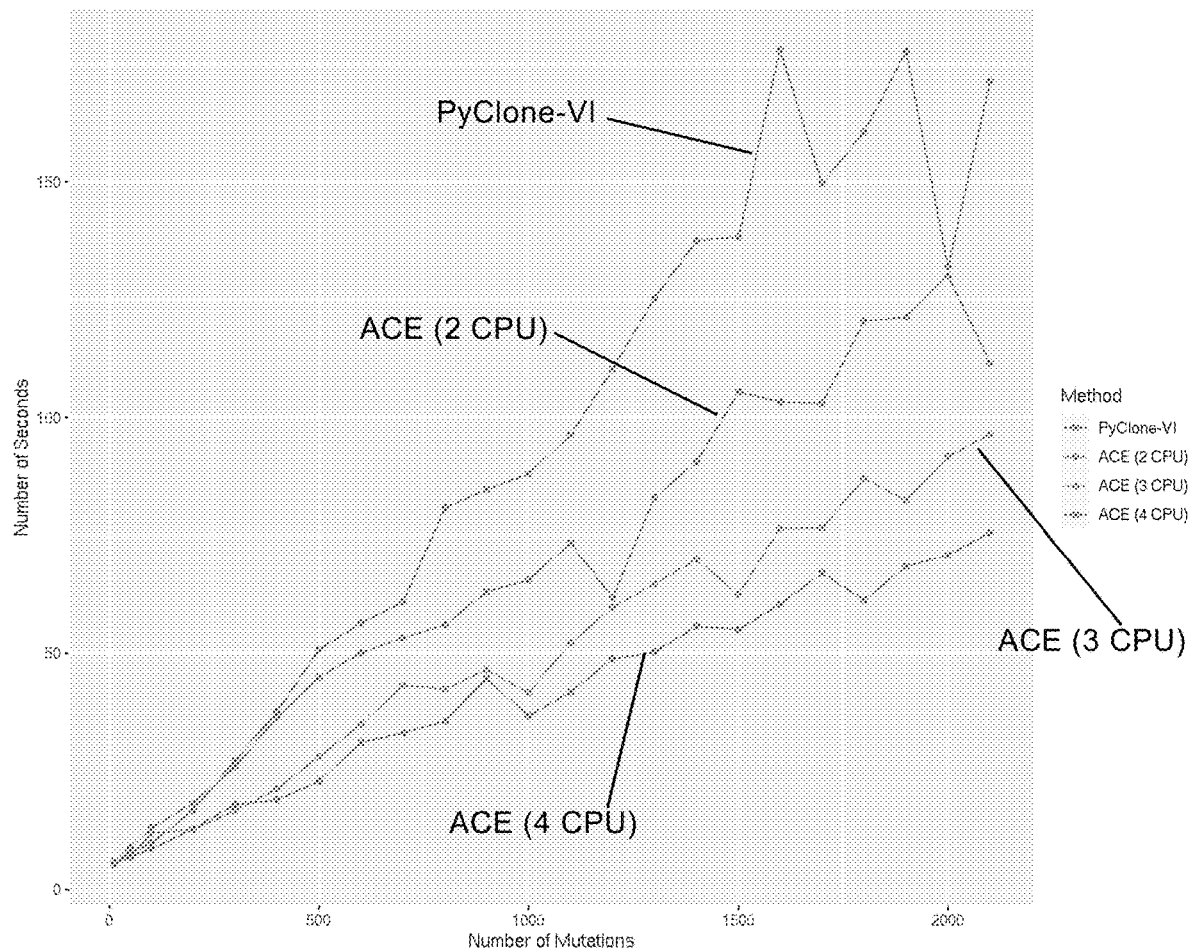
FIG. 8 shows the results of a runtime comparison between a method as described herein and a comparative method. The comparative method (PyClone-VI) has been heavily optimised for computational efficiency but cannot be parallelized. The method described herein (ACE) has not been the subject of extensive computational efficiency optimisation but is more efficient and parallelisable by design (shown implemented with 2, 3 or 4 CPUs).

The methods described herein were formally timed alongside the latest version of PyClone (PyClone-VI, Gills & Roth, BMC Bioinformatics volume 21, Article number: 571 (2020)). The results of this analysis are shown on FIG. 8 (where "ACE" denotes a method as described herein). This version of PyClone has been significantly optimised and is thus faster than the original version used in the informal timing study above. However, because it necessarily analyses all tumour specific mutations identified in a cancer together, the runtime increases significantly as the number of mutations increases, and this cannot be remedied by parallelisation. By contrast, because the methods of the disclosure analyse each mutation independently, there are fully parallelisable. As a result, the runtime associated with the present methods is significantly lower in all cases where the analysis for a single cancer can be run on multiple CPUs (see FIG. 8 which shows results for 2, 3 or 4 CPUs). As an example, for a single patient with between 200 and 1000 mutations, which is a clinically realistic range, the time to identify a probability or being clonal for each mutation using the present methods can be as low as 12.8 seconds-36.5 seconds (respectively for 200 and 1000 mutations). The time to run PyClone-VI by contrast is between 16.8 and 99.1 seconds (respectively for 200 and 1000 mutations). Additionally, this time estimate does not include the time for manual analysis of the clustering structure produced by PyClone to choose a cluster of mutations assumed to be clonal, as well as prioritising mutations within the chosen cluster. By contrast, the methods described herein produce a directly interpretable and independent probability of each mutation being clonal, can be used directly to prioritise mutations (i.e. with no further assessment steps as regards to clonality). This represents a significant saving of resources as well as an increase in process tractability.

Discussion

These examples demonstrate the development and assessment of a new model for identifying mutations which are ubiquitously present across cancer cell populations in a patient, namely clonal mutations. This work has several innovations which significantly improve performance over previous solutions. In particular we recast the problem as a classification problem and provide probabilities for the predictions. This provides the ability to rank mutations instead of previous approaches which returned a binary answer. Furthermore, we show how uncertainty about overlapping copy number can be accounted for. In real world data this leads to a significant increase in performance in terms of precision of identification of clonal mutations. This in practice means that the clonal mutations identified by the methods described herein are more likely to be truly clonal than mutations identified using methods of the prior art, leading to higher validation rates and ultimately higher clinical success rates. Other benefits of the method described herein include the ability to add new mutations without altering the scores of other mutations. Furthermore, the present method is orders of magnitude faster than PyClone and likely other clustering-based approaches.

REFERENCES

Adalsteinsson, V. A., Ha, G., Freeman, S. S. et al. Scalable whole-exome sequencing of cell-free DNA reveals high concordance with metastatic tumors. *Nat Commun* 8, 1324 (2017).

Bulik-Sullivan B, Busby J, Palmer C D, Davis M J, Murphy T, Clark A, Busby M, Duke F, Yang A, Young L, Ojo N C, Caldwell K, Abhyankar J, Boucher T, Hart M G, Makarov V, Montpreville V T, Mercier O, Chan T A, Scagliotti G, Bironzo P, Novello S, Karachaliou N, Rosell R, Anderson I, Gabrail N, Hrom J, Limvarapuss C, Choquette K, Spira A, Rousseau R, Voong C, Rizvi N A, Fadel E, Frattini M, Jooss K, Skoberne M, Francis J, Yelensky R. Deep learning using tumor HLA peptide mass spectrometry datasets improves neoantigen identification. Nat Biotechnol. 2018 Dec. 17.

Carter S L, Cibulskis K, Helman E, McKenna A, Shen H, Zack T, Laird P W, Onofrio R C, Winckler W, Weir B A, Beroukhim R, Pellman D, Levine D A, Lander E S, Meyerson M, Getz G. Absolute quantification of somatic DNA alterations in human cancer. Nat Biotechnol. 2012 May;30 (5):413-21.

Hossein Farahani, Camila P E de Souza, Raewyn Billings, Damian Yap, Karey Shumansky, Adrian Wan, Daniel Lai, Anne-Marie Mes-Masson, Samuel Aparicio, and Sohrab P Shah. Engineered in-vitro cell line mixtures and robust evaluation of computational methods for clonal decomposition and longitudinal dynamics in cancer. Scientific Reports, 7(1):13467, 2017.

Vanessa Jurtz, Sinu Paul, Massimo Andreatta, Paolo Marcatili, Bjoern Peters and Morten Nielsen. NetMHCpan-4.0: Improved Peptide—MHC Class I Interaction Predictions Integrating Eluted Ligand and Peptide Binding Affinity Data. J Immunol Nov. 1, 2017, 199 (9) 3360-3368.

Langmead, B., Trapnell, C., Pop, M. et al. Ultrafast and memory-efficient alignment of short DNA sequences to the human genome. Genome Biol 10, R25 (2009).

Lundegaard C, Lamberth K, Harndahl M, Buus S, Lund O, Nielsen M. NetMHC-3.0: accurate web accessible predictions of human, mouse and monkey MHC class I affinities for peptides of length 8-11. Nucleic Acids Res. 2008 Jul. 1;36(Web Server issue):W509-12.

Nicholas McGranahan, Francesco Favero, Elza C de Bruin, Nicolai Juul Birkbak, Zoltan Szallasi, and Charles Swanton. Clonal status of actionable driver events and the timing of mutational processes in cancer evolution. Science translational medicine, 7(283):283ra54-283ra54, 2015.

McGranahan, N., Furness, A. J., Rosenthal, R., Ramskov, S., Lyngaa, R., Saini, S. K., Jamal-Hanjani, M., Wilson, G. A., Birkbak, N. J., Hiley, C. T., Watkins, T. B., Shafi, S., Murugaesu, N., Mitter, R., Akarca, A. U., Linares, J., Marafioti, T., Henry, J. Y., Van Allen, E. M., Miao, D., . . . Swanton, C. (2016). Clonal neoantigens elicit T cell immunoreactivity and sensitivity to immune checkpoint blockade. Science (New York, N.Y.), 351(6280), 1463-1469.

Timothy J. O'Donnell, Alex Rubinsteyn, Maria Bonsack, Angelika B. Riemer, Uri Laserson, Jeff Hammerbacher. MHCflurry: Open-Source Class I MHC Binding Affinity Prediction. Cell Systems Vol. 7, Issue 1, 129-132, Jul. 25, 2018.

Andrew Roth, Jaswinder Khattra, Damian Yap, Adrian Wan, Emma Laks, Justina Biele, Gavin Ha, Samuel Aparicio, Alexandre Bouchard-Côté, and Sohrab P Shah. PyClone: statistical inference of clonal population structure in cancer. Nature methods, 11(4):396, 2014.

Russell Schwartz and Alejandro A Schäffer. The evolution of tumour phylogenetics: principles and practice. Nature Reviews Genetics, 18(4):213, 2017.

Van Loo P, Nordgard S H, Lingjærde O C, Russnes H G, Rye I H, Sun W, Weigman V J, Marynen P, Zetterberg A, Naume B, Perou C M, Børresen-Dale A L, Kristensen V N. Allele-specific copy number analysis of tumors. Proc Natl Acad Sci USA. 2010 Sep. 28;107(39):16910-5.

Landau D A, Carter S L, Stojanov P, McKenna A, Stevenson K, Lawrence M S, Sougnez C, Stewart C, Sivachenko A, Wang L, Wan Y, Zhang W, Shukla S A, Vartanov A, Fernandes S M, Saksena G, Cibulskis K, Tesar B, Gabriel S, Hacohen N, Meyerson M, Lander E S, Neuberg D, Brown J R, Getz G, Wu C J. Evolution and impact of subclonal mutations in chronic lymphocytic leukemia. Cell. 2013 Feb. 14;152(4):714-26. doi: 10.1016/j.cell.2013.01.019.

Raine K M, Van Loo P, Wedge D C, Jones D, Menzies A, Butler A P, Teague J W, Tarpey P, Nik-Zainal S, Campbell P J. ascatNgs: Identifying Somatically Acquired Copy-Number Alterations from Whole-Genome Sequencing Data. Curr Protoc Bioinformatics. 2016 Dec. 8;56:15.9.1-15.9.17. doi: 10.1002/cpbi.17.

Litchfield K, Reading J L, Puttick C, Thakkar K, Abbosh C, Bentham R, Watkins T B K, Rosenthal R, Biswas D, Rowan A, Lim E, Al Bakir M, Turati V, Guerra-Assunção J A, Conde L, Furness A J S, Saini S K, Hadrup S R, Herrero J, Lee S H, Van Loo P, Enver T, Larkin J, Hellmann M D, Turajlic S, Quezada S A, McGranahan N, Swanton C. Meta-analysis of tumor- and T cell-intrinsic mechanisms of sensitization to checkpoint inhibition. Cell. 2021 Feb. 4;184 (3):596-614.e14.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Various modifications and variations of the described compositions, methods, and uses of the technology will be apparent to those skilled in the art without departing from the scope and spirit of the technology as described. Any sub-titles herein are included for convenience only and are not to be construed as limiting the disclosure in any way.

The methods of any embodiments described herein may be provided as computer programs or as computer program products or computer readable media carrying a computer program which is arranged, when run on a computer, to perform the method(s) described above.

Unless context dictates otherwise, the descriptions and definitions of the features set out above are not limited to any particular aspect or embodiment of the invention and apply equally to all aspects and embodiments which are described.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

The invention claimed is:

1. A method of treating a subject that has been diagnosed as having cancer, the method comprising:
   identifying one or more clonal neoantigens by:
      identifying a plurality of tumour-specific mutations in the subject;
      determining whether one or more of the tumour-specific mutations is likely to be clonal in the subject;
      selecting one or more of the tumour-specific mutations as candidate clonal neoantigens, wherein a candidate clonal neoantigen is a tumour-specific mutation that satisfies at least one or more predetermined criteria on whether the tumour-specific mutation is likely to be clonal; and
   treating the subject with an immunotherapy that targets one or more of the selected candidate clonal neoantigens;
   wherein determining whether a tumour-specific mutation is likely to be clonal in a subject, comprises:
      obtaining, by a processor, sequence data from one or more samples from the subject comprising tumour genetic material, the sequence data comprising for each of the one or more samples, at least two of: the number of reads in the sample that show the tumour-specific mutation ($d_b$), the number of reads in the sample that show the corresponding germline allele, and the total number of reads at the location of the tumour-specific mutation (d), and
      determining, by the processor, a posterior probability that the tumour-specific mutation is clonal depending on: a prior probability of the mutation being clonal, a probability of observing the sequence data if the tumour-specific mutation is clonal, and a probability of observing the sequence data if the tumour-specific mutation is non-clonal, in view of a tumour fraction for each of the one or more samples and one or more candidate joint genotypes each comprising a genotype at the location of the tumour-specific mutation for a normal population, a reference tumour population that does not comprise the tumour-specific mutation and a variant tumour cell population that comprises the tumour-specific mutation.

2. The method of claim 1, wherein the candidate clonal neoantigens are tumour-specific mutations that further satisfy at least one or more predetermined criteria on whether the tumour-specific mutation is likely to give rise to a neoantigen.

3. The method of claim 2, wherein the step of selecting, by said processor, one or more of the tumour-specific mutations as candidate clonal neoantigens, comprises determining, by said processor, whether the one or more tumour specific mutations satisfy one or more criteria on whether the tumour-specific mutation is likely to give rise to a neoantigen selected from: the mutation being associated with an expression product that is expressed in tumour cells, the mutation being predicted to result in a protein or peptide that is not expressed in the normal cells of the subject, the mutation being predicted to result in at least one peptide that is likely to be presented by an MHC molecule, the mutation being predicted to result in at least one peptide that is likely to be presented by an MHC allele that is known to be present in the subject, and the mutation being predicted to result in a protein or peptide that is immunogenic.

4. The method of claim 1, wherein the step of selecting, by said processor, one or more of the tumour-specific mutations as candidate clonal neoantigens, comprises determining, by said processor, whether the one or more tumour specific mutations satisfy one or more predetermined criteria on whether the tumour-specific mutation is likely to be clonal selected from: the mutation having a posterior probability of being clonal above a predetermined threshold, the mutation having a posterior probability of being clonal that is above a threshold set adaptively to select a predetermined number of tumour-specific mutations with the highest posterior probabilities of being clonal amongst the tumour-specific mutations for which a posterior probability was determined, and having a posterior probability of being clonal that is above a threshold set adaptively to select a predetermined top percentile of tumour-specific mutations amongst the tumour-specific mutations for which a posterior probability was determined.

5. The method of claim 1, wherein the immunotherapy that targets the one or more of the selected clonal neoantigens is an immunogenic composition, a composition comprising immune cells or a therapeutic antibody.

6. The method of claim 5, wherein the immunotherapy is a composition comprising T cells that recognise at least one of the one or more selected clonal neoantigens.

7. The method of claim 6, wherein said composition is enriched for T cells that target at least one of the one or more selected clonal neoantigens, or wherein the method comprises obtaining a population of T cells and expanding the population of T cells to increase the number or relative proportion of T cells that target at least one of the one or more selected clonal neoantigens identified.

8. The method of claim 1, wherein the probability of observing the sequence data in view of a tumour fraction in each sample and one or more candidate joint genotypes depends on the probability of observing the sequence data conditional on a tumour fraction, cancer cell fraction and one or more candidate joint genotypes ($Pr(d, db|\pi, \phi, t)$).

9. The method of claim 8, wherein the probability of observing the sequence data in view of a tumour fraction, cancer cell fraction and one or more candidate joint genotypes is a weighted sum of the probabilities of observing the sequence data in view of a tumour fraction, cancer cell fraction and each of the one or more candidate joint genotypes.

10. The method of claim 1, wherein the probability of observing the sequence data in view of a tumour fraction in each sample and one or more candidate joint genotypes is obtained as an integral over all possible values of the cancer cell fraction in each sample, wherein the cancer cell fraction is the proportion of tumour cells that comprise the tumour-specific mutation.

11. The method of claim 10, wherein the step of determining, by the processor, the posterior probability that the tumour-specific mutation is clonal comprises using the processor to numerically integrate said integral.

12. The method of claim 1, wherein obtaining, by the processor, sequence data from one or more samples comprises obtaining sequence data from a plurality of samples and wherein the probability of observing the sequence data in view of a tumour fraction for each of the plurality of samples and one or more candidate joint genotypes is obtained as the product of the probability of observing the sequence data of each sample in view of the tumour fraction in the respective sample and the one or more candidate joint genotypes.

13. The method of claim 1, wherein obtaining, by the processor, sequence data from one or more samples comprises the processor receiving sequence data comprising sequence reads for the one or more samples and determining from said sequence reads at least two of: the number of reads in the sample that show the tumour-specific mutation ($d_b$), the number of reads in the sample that show the corresponding germline allele, and the total number of reads at the location of the tumour-specific mutation (d).

14. The method of claim 1, further comprising obtaining, for each sample, at least one estimate of the tumour fraction, and at least one corresponding set of one or more candidate joint genotypes.

15. The method of claim 14, wherein obtaining, for each sample, at least one estimate of the tumour fraction comprises the processor determining an estimate of the tumour fraction and allele specific copy numbers using the sequence data, and determining a set of one or more candidate joint genotypes associated with said allele specific copy numbers.

16. The method claim 1, wherein the probability of observing the sequence data combines a plurality of probabilities of observing the sequence data in view of a respective tumour fraction and a corresponding set of one or more candidate joint genotypes for at least one or the one or more samples.

17. The method of claim 16, wherein the method comprises obtaining, for at least one or the one or more samples, a plurality of estimates of the tumour fraction, and a plurality of corresponding sets of one or more candidate joint genotypes.

18. The method of claim 17, wherein obtaining, for at least one sample, a plurality of estimates of the tumour fraction comprises the processor determining a plurality of estimates of the tumour fraction and a corresponding plurality of allele specific copy numbers that are compatible with the sequence data, and determining a plurality of sets of one or more candidate joint genotypes associated with said plurality of allele specific copy numbers.

19. The method of claim 1, wherein the prior probability of the mutation being clonal is set to a neutral prior, or to a value derived from prior data and/or expert knowledge.

20. The method of claim 1, wherein identifying one or more tumour-specific mutations in the subject comprises comparing sequence data from one or more samples from the subject comprising tumour genetic material and sequence data from one or more germline samples from the subject.

* * * * *

UNITED STATES PATENT AND TRADEMARK OFFICE
CERTIFICATE OF CORRECTION

| | | |
|---|---|---|
| PATENT NO. | : 11,504,398 B2 | Page 1 of 1 |
| APPLICATION NO. | : 17/711372 | |
| DATED | : November 22, 2022 | |
| INVENTOR(S) | : Andrew Roth et al. | |

It is certified that error appears in the above-identified patent and that said Letters Patent is hereby corrected as shown below:

On the Title Page

Item [30]:
"Apr 1. 2021 (GB)................ 2104715"
Should read:
--Apr 1. 2021 (GB)................ 2104715.4--

Signed and Sealed this
Seventeenth Day of January, 2023

Katherine Kelly Vidal
*Director of the United States Patent and Trademark Office*